US007143765B2

(12) United States Patent
Asking et al.

(10) Patent No.: US 7,143,765 B2
(45) Date of Patent: Dec. 5, 2006

(54) INHALATION DEVICE

(75) Inventors: Lars Asking, Lund (SE); Ian Harwigsson, Malmö (SE); Mikael Jonströmer, Lund (SE)

(73) Assignee: AstraZeneca AB, Sodertalje (SE)

( * ) Notice: Subject to any disclaimer, the term of this patent is extended or adjusted under 35 U.S.C. 154(b) by 68 days.

(21) Appl. No.: 10/478,395

(22) PCT Filed: May 21, 2002

(86) PCT No.: PCT/SE02/00990

§ 371 (c)(1),
(2), (4) Date: Nov. 19, 2003

(87) PCT Pub. No.: WO02/094357

PCT Pub. Date: Nov. 28, 2002

(65) Prior Publication Data

US 2004/0168687 A1    Sep. 2, 2004

(30) Foreign Application Priority Data

May 22, 2001 (SE) .................................. 0101825

(51) Int. Cl.
*A61M 15/00* (2006.01)
*A61M 11/00* (2006.01)
(52) U.S. Cl. .............................. 128/203.15; 128/203.21
(58) Field of Classification Search ........... 128/203.12, 128/203.15, 203.21, 203.23, 204.17, 200.23, 128/202.21, 203.11, 204.12, 204.13, 200.14, 128/200.19; 131/194, 195
See application file for complete search history.

(56) References Cited

U.S. PATENT DOCUMENTS

| 2,534,636 | A | * | 12/1950 | Stirn ...................... 128/203.15 |
| 2,603,215 | A | * | 7/1952 | Arnow .................. 128/203.15 |
| 2,693,805 | A | * | 11/1954 | Taplin et al. .......... 128/203.15 |
| 3,888,252 | A | * | 6/1975 | Side et al. ............. 128/203.15 |
| 5,201,308 | A | * | 4/1993 | Newhouse ............. 128/203.15 |
| 5,351,683 | A |   | 10/1994 | Chiesi et al. .......... 128/203.12 |
| 5,746,227 | A |   | 5/1998 | Rose et al. |
| 5,778,873 | A | * | 7/1998 | Braithwaite ............ 128/203.15 |

(Continued)

FOREIGN PATENT DOCUMENTS

DE          199 63 946          7/2001

(Continued)

OTHER PUBLICATIONS

English Abstract of SU 1597195.

(Continued)

*Primary Examiner*—Teena Mitchell
(74) *Attorney, Agent, or Firm*—Fish & Richardson P.C.

(57) ABSTRACT

An inhalation device for delivery of a powdered medicament comprising a suction tube (21) and one or more doses of powdered medicament. The suction tube (21) has a distal end (28) and a proximal end (29) with an air passage (30) therethrough, the distal end (28) having an air inlet and the proximal end (29) having an air outlet which forms the mouthpiece of the device. The inhalation device further comprises a means for drying air (23) drawn by a user into the inhalation device prior to contact with the aggregated powdered medicament such that a dose of powdered medicament will be dispersed in dried air for delivery at the proximal end.

19 Claims, 37 Drawing Sheets

U.S. PATENT DOCUMENTS

| | | |
|---|---|---|
| 6,520,179 B1 * | 2/2003 | Von Schuckmann et al. ............ 128/203.15 |
| 6,595,209 B1 * | 7/2003 | Rose et al. ............ 128/203.15 |
| 6,715,485 B1 * | 4/2004 | Djupesland ............ 128/203.15 |
| 6,892,728 B1 * | 5/2005 | Helgesson et al. ..... 128/203.15 |
| 2003/0140923 A1 * | 7/2003 | Taylor et al. ........... 128/203.12 |
| 2004/0089299 A1 * | 5/2004 | Bonney et al. ......... 128/203.15 |
| 2005/0183723 A1 * | 8/2005 | Pinon et al. ............ 128/203.15 |

FOREIGN PATENT DOCUMENTS

| | | |
|---|---|---|
| SU | 1597195 | 10/1990 |
| WO | WO 89/01348 | 2/1989 |
| WO | WO 92/04069 | 3/1992 |
| WO | WO 97/40876 | 11/1997 |
| WO | WO 98/41256 | 9/1998 |
| WO | WO 99/31952 | 7/1999 |

OTHER PUBLICATIONS

Copy of a communication from a foreign patent office in a counterpart application.

* cited by examiner

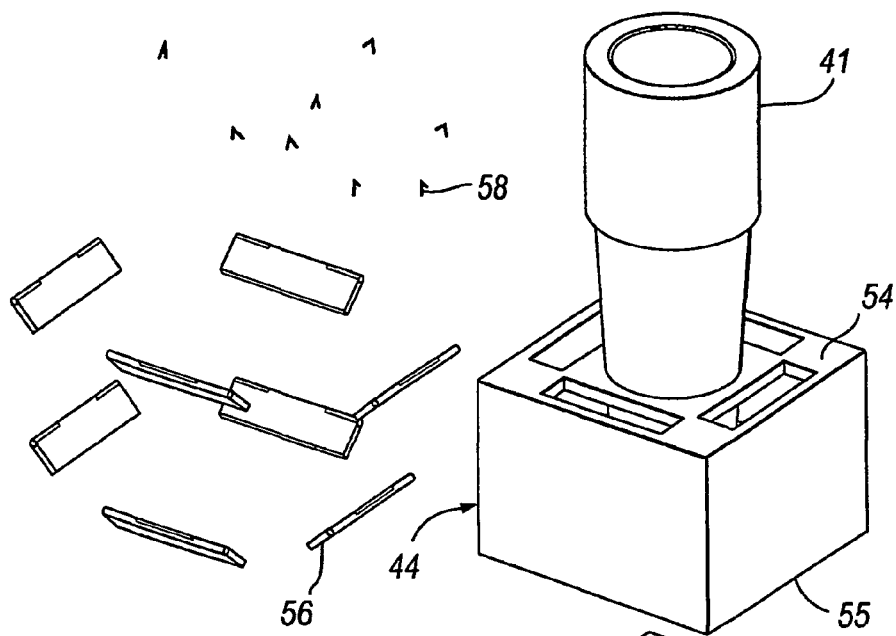
Fig.10
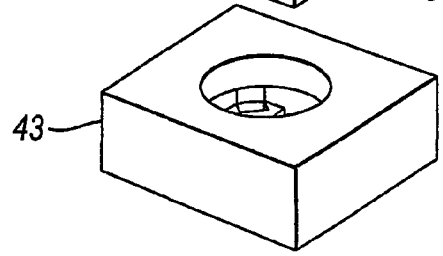
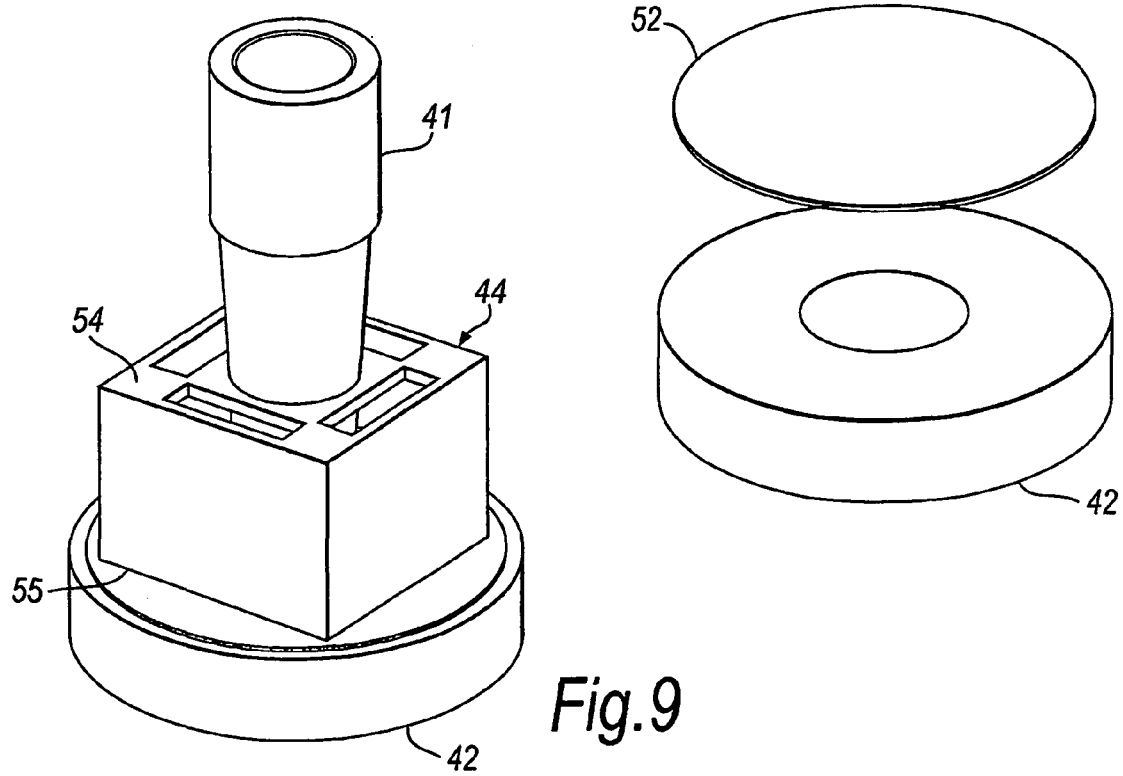
Fig.9

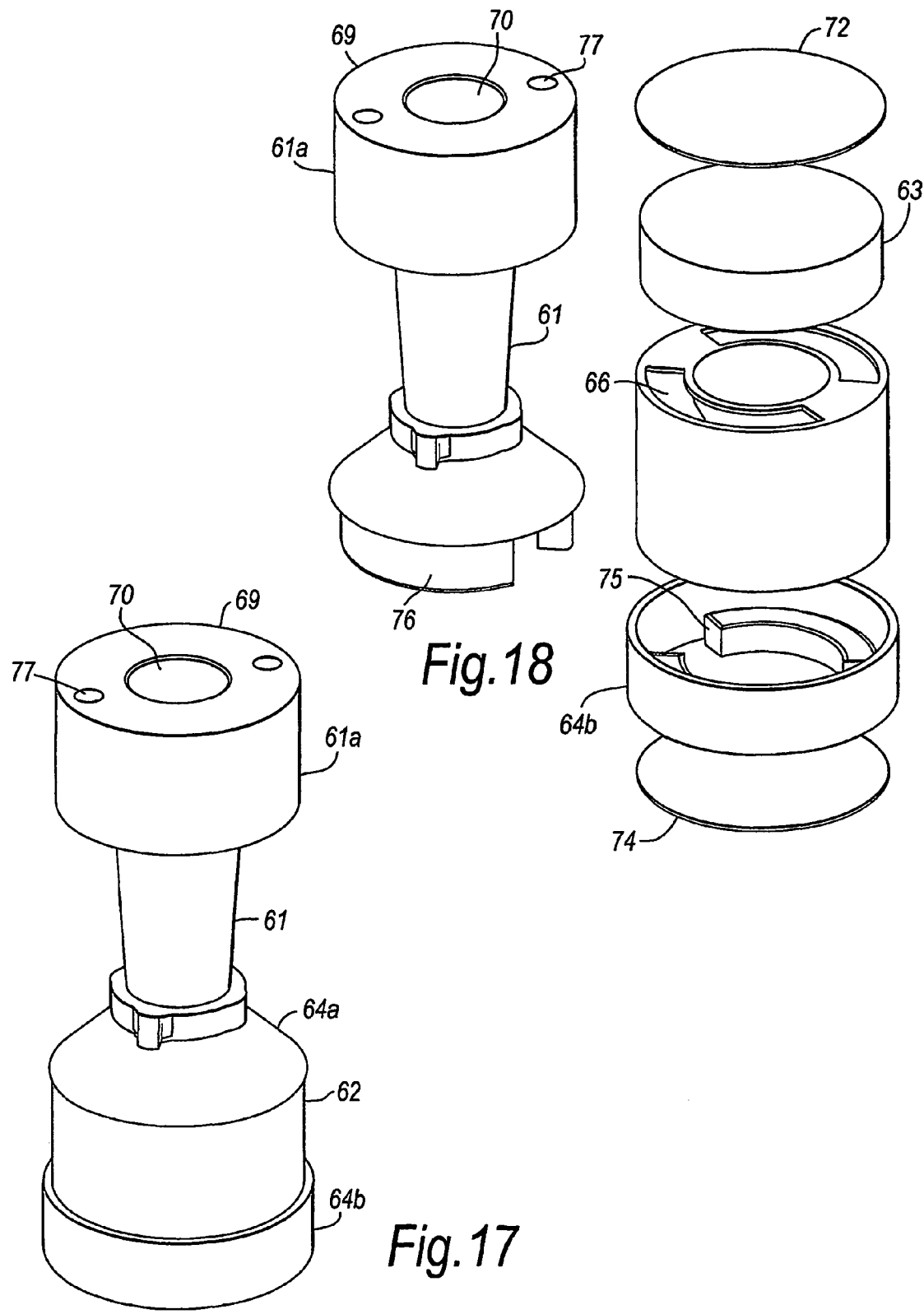

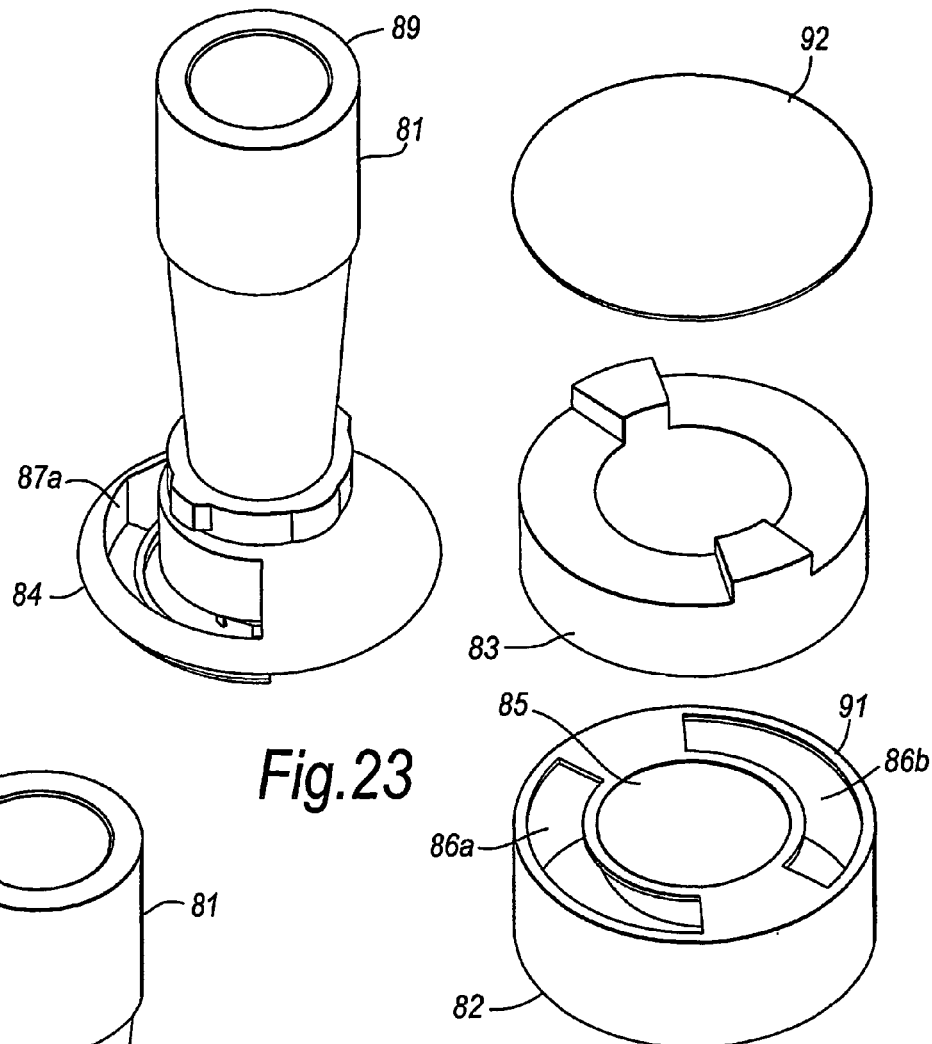
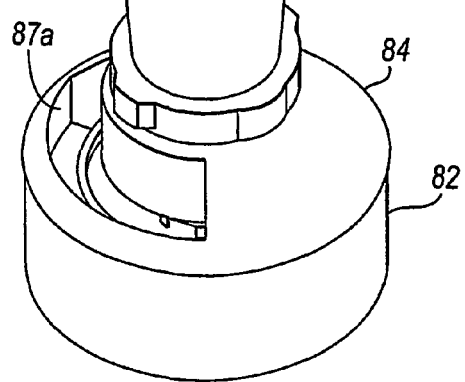
Fig. 23
Fig. 22

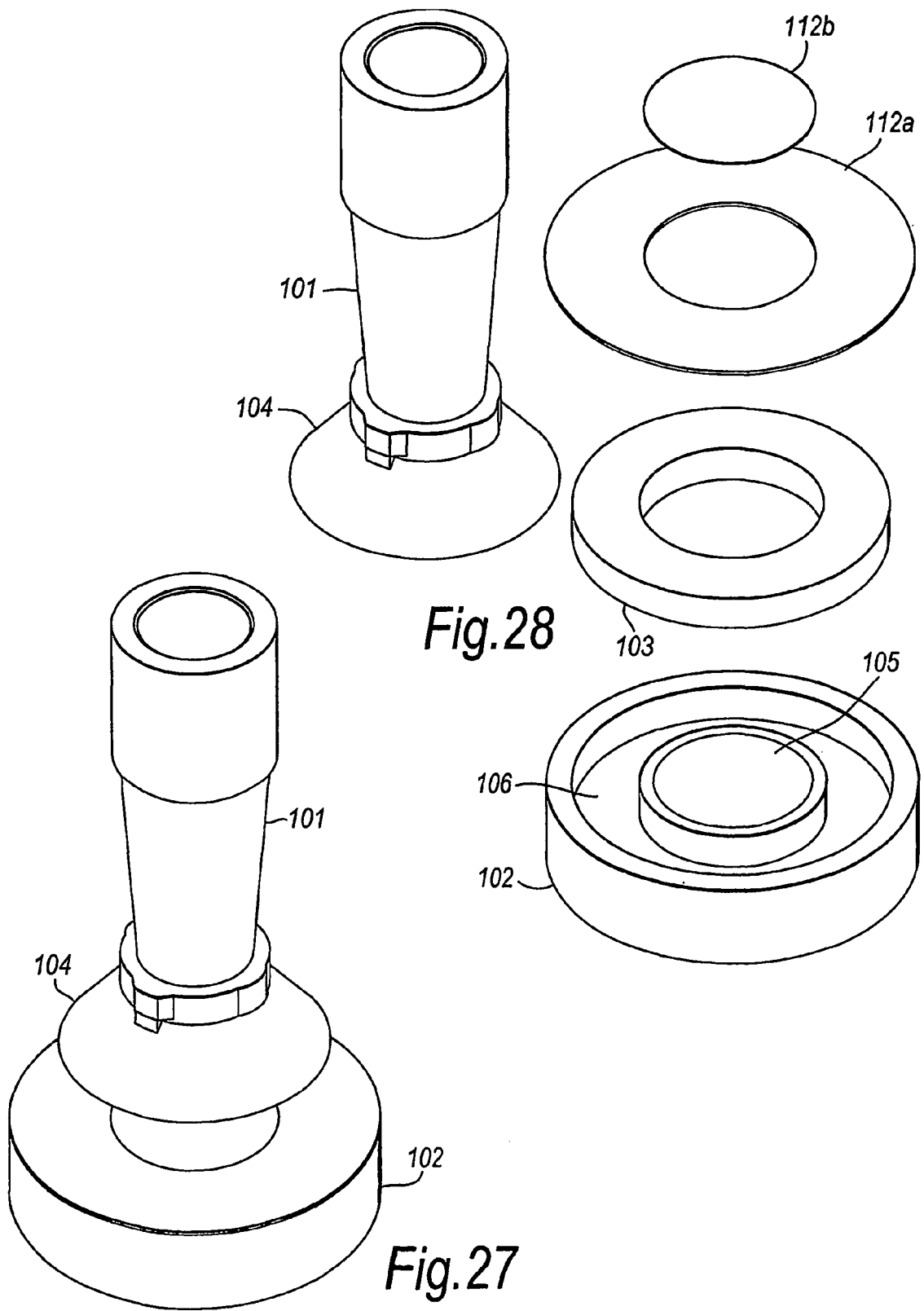

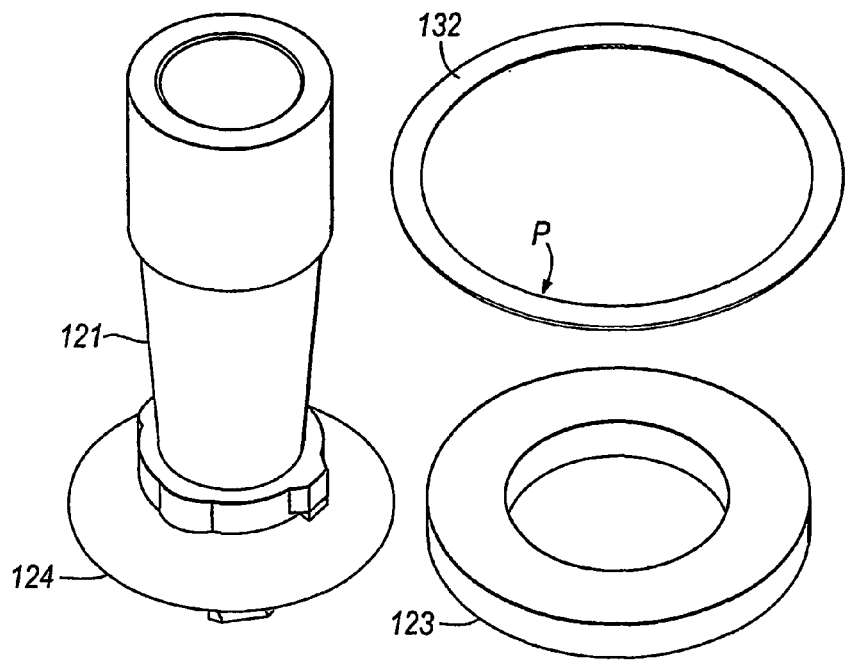
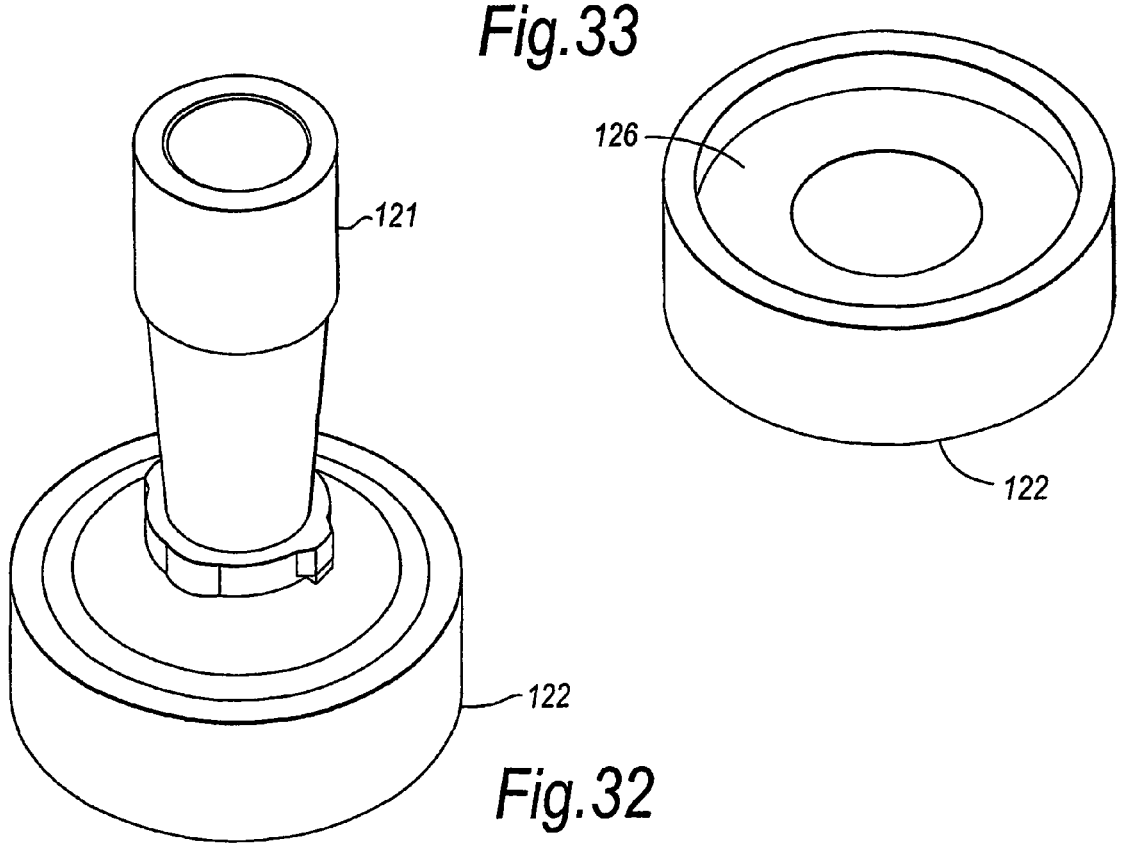
Fig.33
Fig.32

INHALATION DEVICE

CROSS-REFERENCE TO RELATED APPLICATIONS

This application is the national phase application under 35 U.S.C. § 371 of PCT International Application No. PCT/SE02/00990 which has an International filing date of May 21, 2002, which designated Swedish Application Serial No. 0101825-8, filed May 22, 2001 as priority, the contents of which are incorporated by reference in their entirety.

TECHNICAL FIELD

The present invention relates to an inhalation device for delivery of a powdered medicament, generally referred to as a dry powder inhaler (DPI) and used for local and systemic administration, particularly in the treatment of respiratory conditions.

BACKGROUND

Several types of dry powder inhalers are known and in this respect reference should be made to WO 97/40876, WO 98/41256 and WO 92/04069 which disclose examples of such inhalers.

WO 97/40876 describes an inhalation device comprising a suction tube and blister pack assembly. The blister pack assembly is in the form of a carrier or support unit which holds the blister pack. The carrier or support unit is configured such that the upper surface has a plurality of holes which sit above the blisters in the blister pack. Accordingly, the distal end of the suction tube can be placed in a blister when the user needs to inhale the powdered medicament.

WO 98/41256 describes an inhalation device which is known as the TURBUHALER®. This inhalation device has a dosing means which is operated by twisting a rotatable gripping portion. The twisting action releases a dose of powdered medicament into a dosing unit which can then be inhaled by the user.

WO 92/04069 describes an inhalation device which is known as the MONOHALER® delivering only a single dose of powdered medicament. The powdered medicament is released by removing sealing foil portions and is then simply inhaled by the user inhaling through the mouthpiece.

Dry powder inhalers (DPI's) have many advantages over inhalers such as pressurised metered dose inhalers (PMDI's). For example, no propellants are needed, pure drug administration is possible and they are relatively simple to operate. However, a disadvantage encountered in dry powder inhalers is their sensitivity to moisture. Some dry powder formulations suffer negative effects when the humidity in the air inhaled through the inhalation device increases. In particular, the relative humidity (RH) will result in an increase in retention of the powder formulation in the inhalation device. At high relative humidity the water molecules in the humid air will react with the surface of the particles of the powder formulation during the short time it takes for the incoming inhaled air to move or lift and deaggregate the powder.

SUMMARY

Whilst the powder formulation could be processed, e.g. conditioned to reduce its reaction with water molecules in the humid air, it has been discovered through experimentation that one of the most efficient ways to reduce the negative effects of humidity is to dry out the incoming air prior to contact with the aggregated powder formulation so that a dose of powdered medicament will be dispersed in dried air for subsequent inhalation by the user.

The negative effects of humidity occur both in the short term and the long term. The short term effects are the decrease in aerosol quality, e.g. difficulties with deaggregation of powder (in both spheronized and ordered mixtures) and the retention of the powder formulation in the inhalation device. The long term effects arise as a result of physical and/or chemical degradation of the powder formulation mainly due to contact with water. For example, water will normally be introduced to the powder formulation due to handling before and during filling of the inhalation device and during storage by permeation through the packaging. In the case of multi-dose reservoir-type inhalation devices such as the TURBUHALER®, water can also accumulate during each dose delivery. Clearly, any drying capacity introduced into the inhalation device may also be used to keep the powder formulation dry and thus avoid chemical degradation. It would also be possible to fill the inhalation device under humid conditions and then dry the contents after filling.

A measure of how effective an inhalation device is can be obtained by monitoring the fine particle fraction (FPF), i.e. the fraction of particles which have an aerodynamic diameter of less than 5 mm. In general, only fine particles are effective in reaching the part of the body at which the powder formulation is directed since the larger particles will not be dispersed properly and will not be able to travel with the inhaled air to the treatment or absorption zone. The FPF as a percentage of the dose of powder formulation decreases significantly as the relative humidity (RH) increases. In this respect, reference should now be made to FIG. 1A which is a graphic depiction of the variation of FPF with increasing RH for a typical moisture sensitive powder formulation. Four different ordered mixtures of powder formulation were monitored.

The retention of the powder formulation in the inhalation device increases with relative humidity (RH) and this can be seen in FIG. 1B for the same four ordered mixtures of powder formulation.

FIG. 1C depicts the increase in chemical degradation after a storage period of six months as the relative humidity increases.

The object of the present invention is to overcome the disadvantages which arise as a result of humidity in dry powder inhalation devices.

According to the present Invention, there is provided an inhalation device for delivery of a powdered medicament comprising a suction channel and one or more doses of powdered medicament, the suction channel having a distal end and a proximal end with an air passage therethrough, the distal end having an air inlet and the proximal end having an air outlet which forms the mouthpiece of the device, wherein the inhalation device further comprises a means for drying air drawn by a user into the inhalation device prior to contact with the aggregated powdered medicament such that a dose of powdered medicament will be dispersed in dried air for delivery at the proximal end.

Preferably, at least part of the volume of the air drawn by the user into the inhalation device passes through the means for drying the air prior to contact with the powdered medicament.

Preferably, the means for drying air is located such that the air is dried prior to entering the air inlet.

Preferably, the suction channel is in the form of a suction tube and the powdered medicament is located outside the suction tube.

Preferably, the powdered medicament is contained in a blister pack having one or more blisters and the suction tube is constructed such that the distal end can penetrate a blister.

Preferably, the inhalation device further comprises a housing having one or more channels therein for directing air inhaled by the user to the air inlet.

Preferably, the means for drying the air is located between the housing and the air inlet.

Preferably, the housing forms part of the suction tube.

Preferably, the means for drying the air is located within the housing.

Preferably, the means for drying the air is located within the blister pack.

Preferably, the housing is partly formed by the suction tube and partly formed by the blister pack.

Preferably, the means for drying the air is located in the blister pack.

Preferably, at least one bypass channel is provided in the mouthpiece to facilitate inhalation by the user.

Preferably, the suction channel is in the form of a suction tube and the powdered medicament is located in a cavity in the suction tube and the means for drying the air is located between the air inlet and the cavity.

DESCRIPTION OF DRAWINGS

Preferred embodiments of the present invention will now be described in detail, by way of example only, with reference to the accompanying drawings, in which:

FIG. 9 is a perspective view of a third preferred embodiment of the present invention;

FIG. 10 is an exploded view of the elements in FIG. 9;

FIG. 17 is a perspective view of a fifth preferred embodiment of the present invention;

FIG. 18 is an exploded view of the elements in FIG. 17;

FIG. 22 is a perspective view of a sixth preferred embodiment of the present invention;

FIG. 23 is an exploded view of the elements in FIG. 22;

FIG. 27 is a perspective view of a seventh preferred embodiment of the present invention;

FIG. 28 is an exploded view of the elements in FIG. 27;

FIG. 32 is a perspective view through an eighth preferred embodiment of the present invention;

FIG. 33 is an exploded view of the elements in FIG. 32;

DETAILED DESCRIPTION

Figure 1:
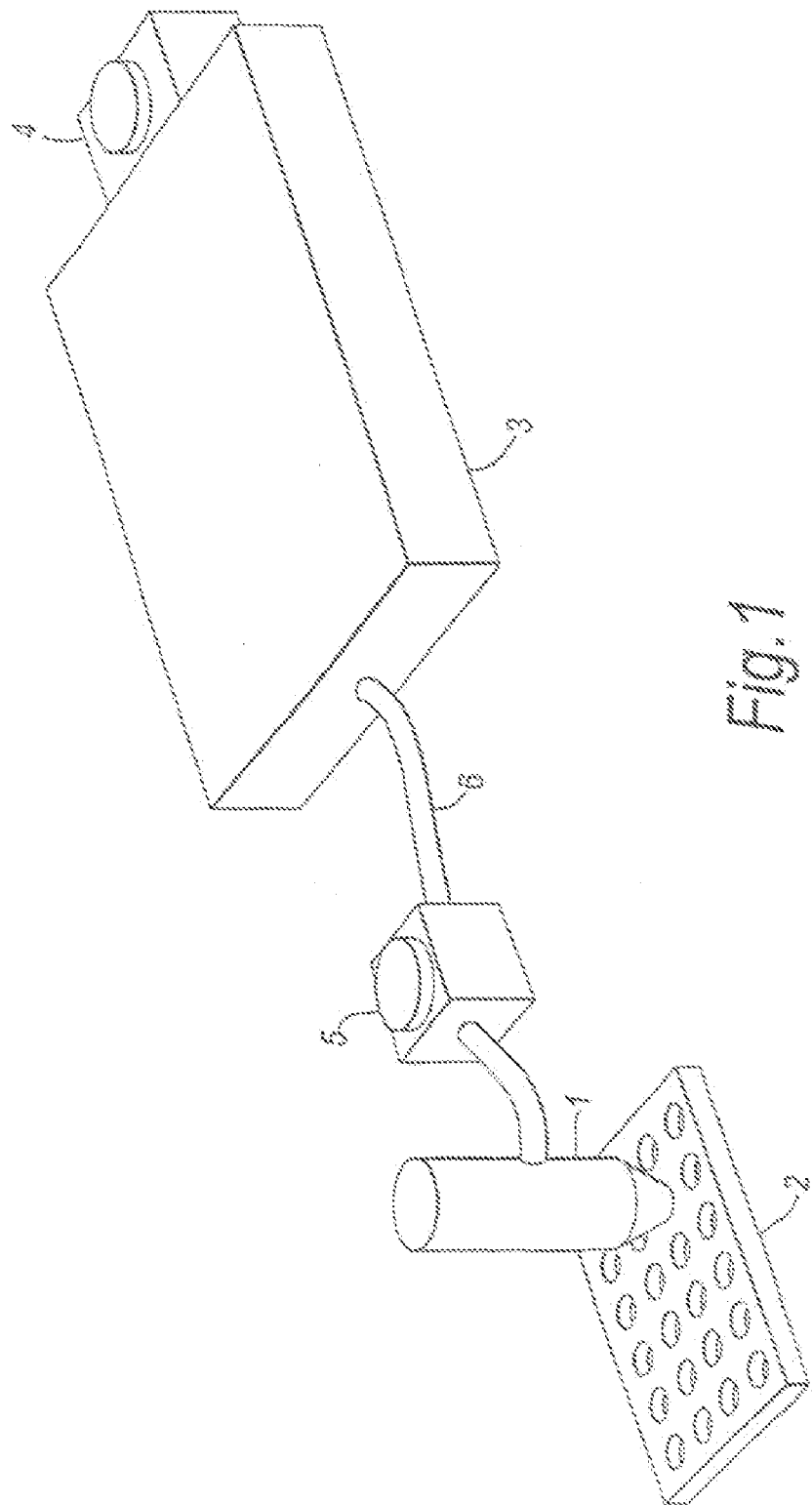
FIG. 1 is a schematic diagram of a first preferred embodiment of an inhalation device according to the present invention.
Figure 1A:
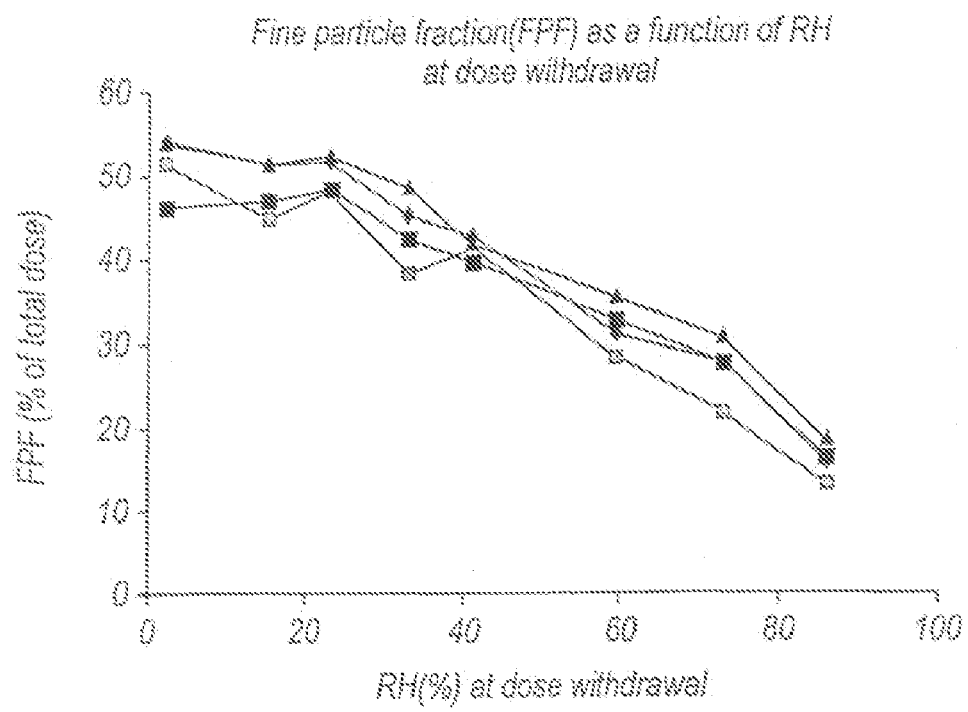
FIG. 1A is a graphic depiction of the variation of fine particle fraction (FPF) with increasing RH.
Figure 1B:
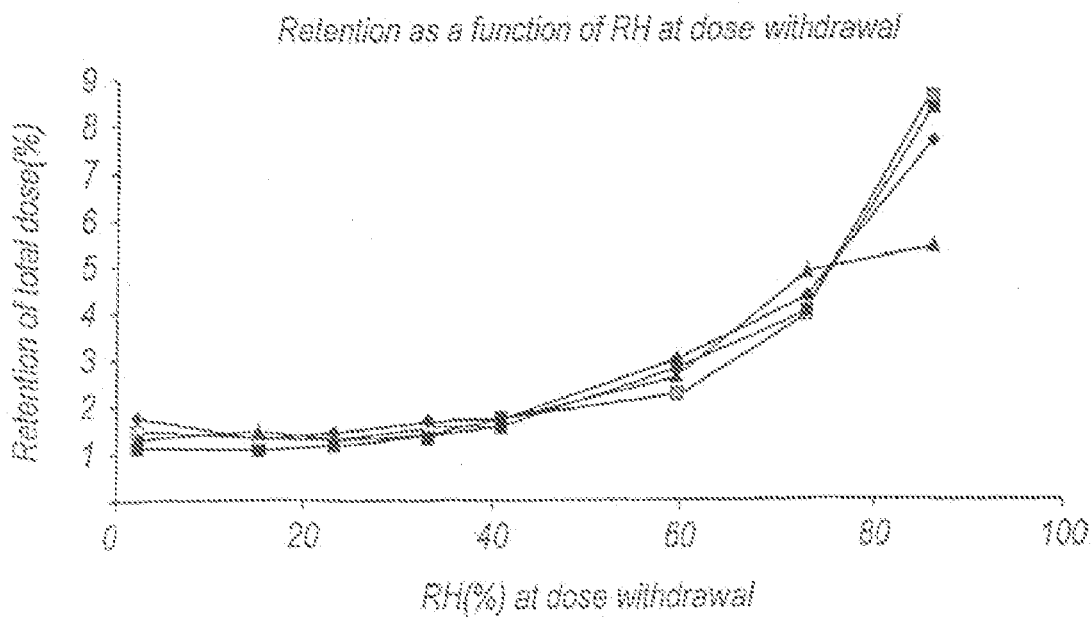
FIG. 1B is a graph of powder retention as a function of relative humidity as dose withdrawal.
Figure 1C:
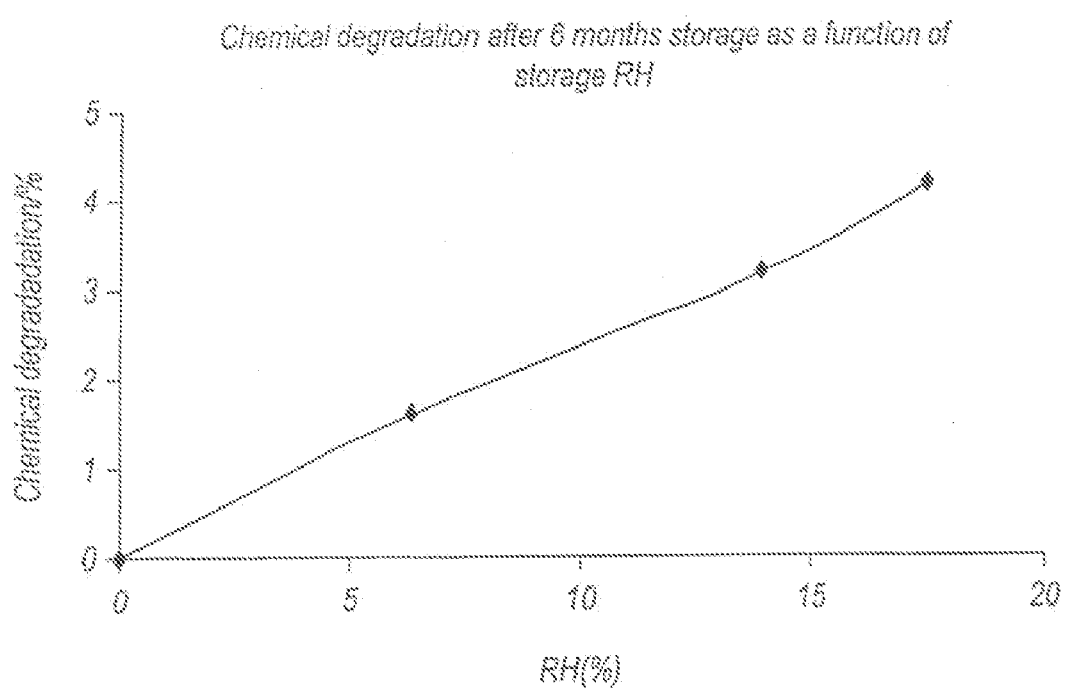
FIG. 1C is a graph of chemical degradation after six months storage as a function of storage relative humidity.

Reference should now be made to FIG. 1 which is a schematic representation of the first preferred embodiment of the inhalation device.

The inhalation device comprises a suction tube 1 and a blister pack 2 holding several doses of a powdered medicament. When the user inhales through the suction tube 1 air will be drawn through a drying box 3 which contains bulk drying agent. The drying box 3 is provided with valves 4 and 5 which ensure that moisture does not enter the drying box 3 when the inhalation device is not in use. Dried air will pass from the drying box 3 through a hose 6 to the suction tube 1.

When a bulk drying agent is used, the inhalation device can be protected during long term storage.e.g. up to 24 months and in some cases even longer. It is not a requirement that all air drawn through the drying box 3 and into the suction tube 1 is dried. The amount of drying required will vary depending upon how sensitive the powder formulation in the blister pack 2 is and also how sensitive the inhalation device is required to be. For example, it may be sufficient to dry only the first fraction of the air inhaled or only reduce the moisture content rather than drying the air completely. In some types of inhalation device, the powder formulation is completely delivered after only a very short time with the initial airflow. Accordingly, only the initial airflow needs to be dried and the remaining airflow can continue without drying until the user completes the inhalation process.

Typically, there will be sufficient bulk drying agent in drying box 3 to dry the air which will be inhaled during emptying of all the blisters in the blister pack 2.

FIG. 2 is a sectional view through the suction tube 1 in FIG. 1 and one blister 7 in the blister pack 2 before penetration of the blister 7.

The suction tube 1 comprises a distal end 8 and a proximal end 9 with an air passage 10 therethrough. The distal end 8 forms the air inlet and the proximal end 9 forms the air outlet which is the mouthpiece of the inhalation device. The distal end 8 comprises a cutting mechanism which typically includes a cutting blade 15*a* and plunger blades 15*b* to push the cut blister 7 fully open and ensure that there is a clear passage for airflow into and out of the cavity 13.

The blister pack 2 comprises a lower base 11 and an upper foil layer 12. The lower base 11 has one or more cavities 13 which hold the powder formulation to be inhaled. The upper foil layer 12 seals the powder formulation within the cavity or cavities 13.

In this embodiment the suction tube 1 comprises a housing 14 around the distal end 8 which directs dried air flowing through hose 6 to the air inlet in the distal end 8.

When the user has penetrated the blister 7, inhalation from the mouthpiece 9 will draw dried air from the drying box 3 through hose 6 into the housing 14, down into the cavity 13 and up through the distal end 8 to finally pass through the air passage 10 to the user. Airflow arrows have been added to FIG. 3 to show the direction of airflow.

Preferably, the housing 14 forms an air-tight chamber above the blister pack 2 to avoid moist air being drawn into contact with the powder formulation in the blister 13. However, the volume within the housing 14 should be minimised because the moist air within this volume will come into contact with the contents of the cavity 13 on penetration.

The valve 5 is a preferred feature which will prevent moist air from passing through the suction tube 1 back into the drying box 3. If included, valve 5 should be placed as close to the suction tube 1 as possible otherwise, moist air will sit within the length of hose 6 between the suction tube 1 and valve 5 which will then pass into the housing 14 when the user next uses the inhalation device. The valves 4 and 5 can be actuated by the user, e.g. mechanical, electrical, magnetic or suction operated or by the action of penetrating the blister 7. Servo motors could be used, for example, or the valves could be actuated by using body heat in combination with shape-memory alloys or bi-metals Suitable forms of drying agent would be all materials that are able to remove water from air, e.g. by binding water or by reacting with water. Solid materials are preferred but materials in all physical states can be used. Materials that are nonhazardous and that do not form hazardous products are preferred as well as materials that do not change physical state. All geometric forms can be used.

The drying material can be used as is or in mixtures. Examples are desiccant powder in a polymer matrix and desiccant powder on the surface of a solid support. Suitable materials are also materials where the material as such has no affinity for water but where the surface can be made hydrophilic by for instance oxidation.

Basically, all materials that have affinity for water may be used as drying materials. Inorganic examples would be Calcium chloride, Calcium oxide, Calcium sulfate, Copper (II) sulfate, Magnesium oxide, Magnesium perchlorate, Magnesium sulfate, Potassium carbonate, Sodium sulfate, Calcium hydride, Lithium aluminium hydride, Potassium hydroxide, Sodium hydroxide, Sodium oxide, Sodium-lead alloy, Phosphor pentoxide, Sulphuric acid, Molecular sieve, Silica gel and Aluminium oxide. Organic examples would be Carbohydrates, Monosaccarides (e.g. glucose, mannose, fructose, and galactose), Disaccarides (e.g. sucrose, lactose, trehalose), Oligosaccarides (e.g. carrageenan, cellulose), Proteins and Lipids.

Other organic materials would be cotton, viscose, starch, paper, silk, wool, and hydrogels (e.g. crosslinked acrylate copolymer).

Suitable mixtures would be polymers (e.g. polypropylene) mixed with desiccant (e.g. silica or molecular sieve), desiccants (e.g. aluminium oxide) on a solid support.

FIGS. 4 to 8 depict various views of the second preferred embodiment. The inhalation device comprises a suction tube 21 and a blister pack 22. A drying agent 23 surrounds the suction tube 21 and is held within a housing 24. The drying agent 23 will typically be capable of drying the air for one or two doses of powder formulation from the blister pack 22. In this embodiment, the blister pack 22 depicted has only a single blister 25. However, the drying agent 23 can be regenerated by placing the inhalation device in a drying box 26 (see FIG. 6) which will be filled with a large bulk of drying agent 27 capable of drying the powder in a multi-dose blister pack.

FIGS. 7 and 8 are sectional views before and after penetration of the blister pack 22. The suction tube 21 comprises a distal end 28 and a proximal end 29 with an air passage 30 therethrough. The distal end 28 forms the air inlet and the proximal end 29 forms the air outlet which is the mouthpiece of the inhalation device.

The blister pack 22 comprises a lower base 31 and an upper foil layer 32. The lower base 31 has one or more moulded cavities 33 which hold the powder formulation to be inhaled. The upper foil 32 seals the powder formulation within the cavity or cavities 33.

In this embodiment, the suction tube 21 comprises an open housing 24 which surrounds the suction tube 21 in the area of the distal end 28.

Figure 2:
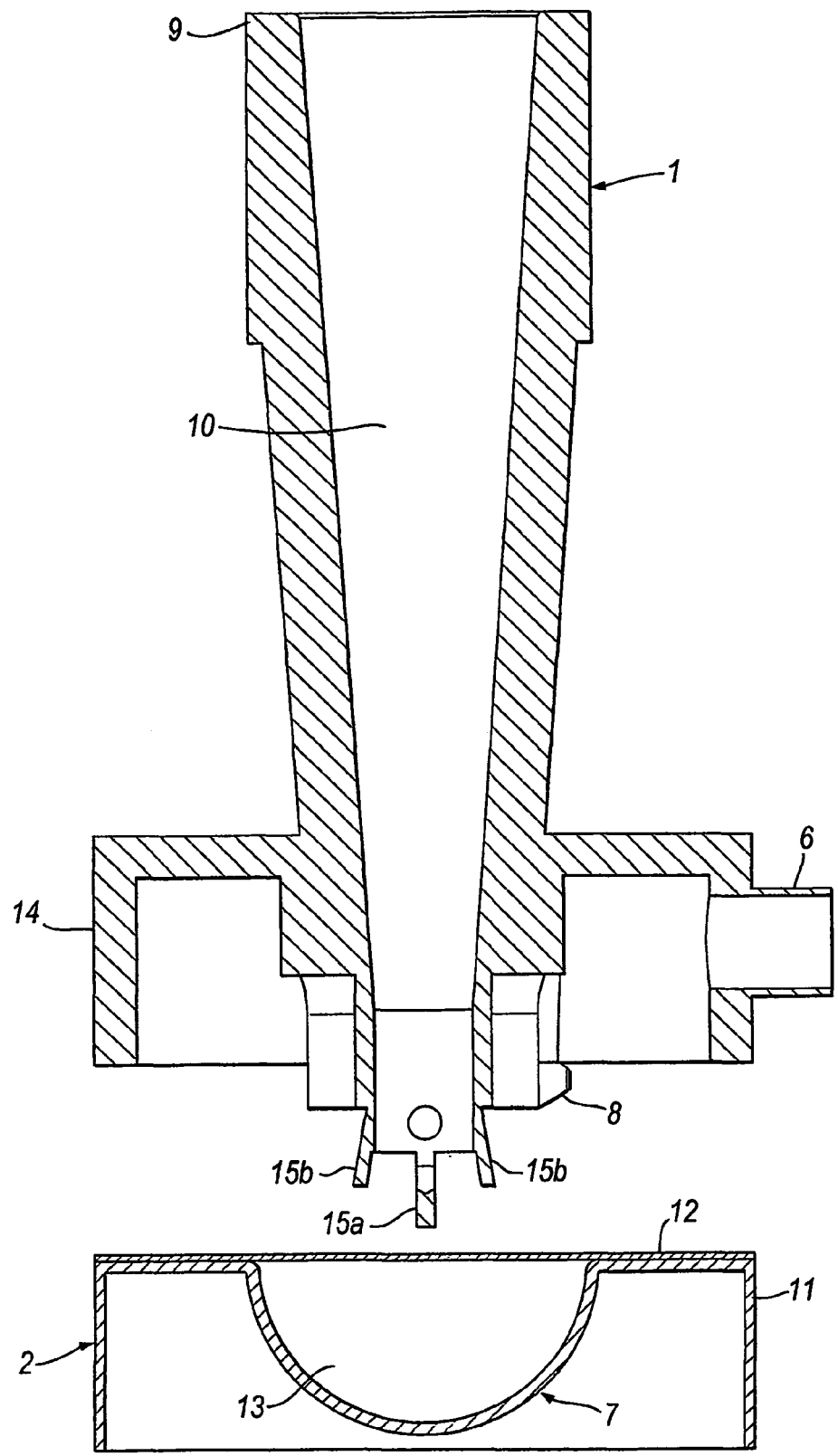
FIG. 2 is a sectional view through the suction tube and blister pack of the inhalation device in FIG. 1 before insertion of the suction tube into the blister pack.
Figure 3:
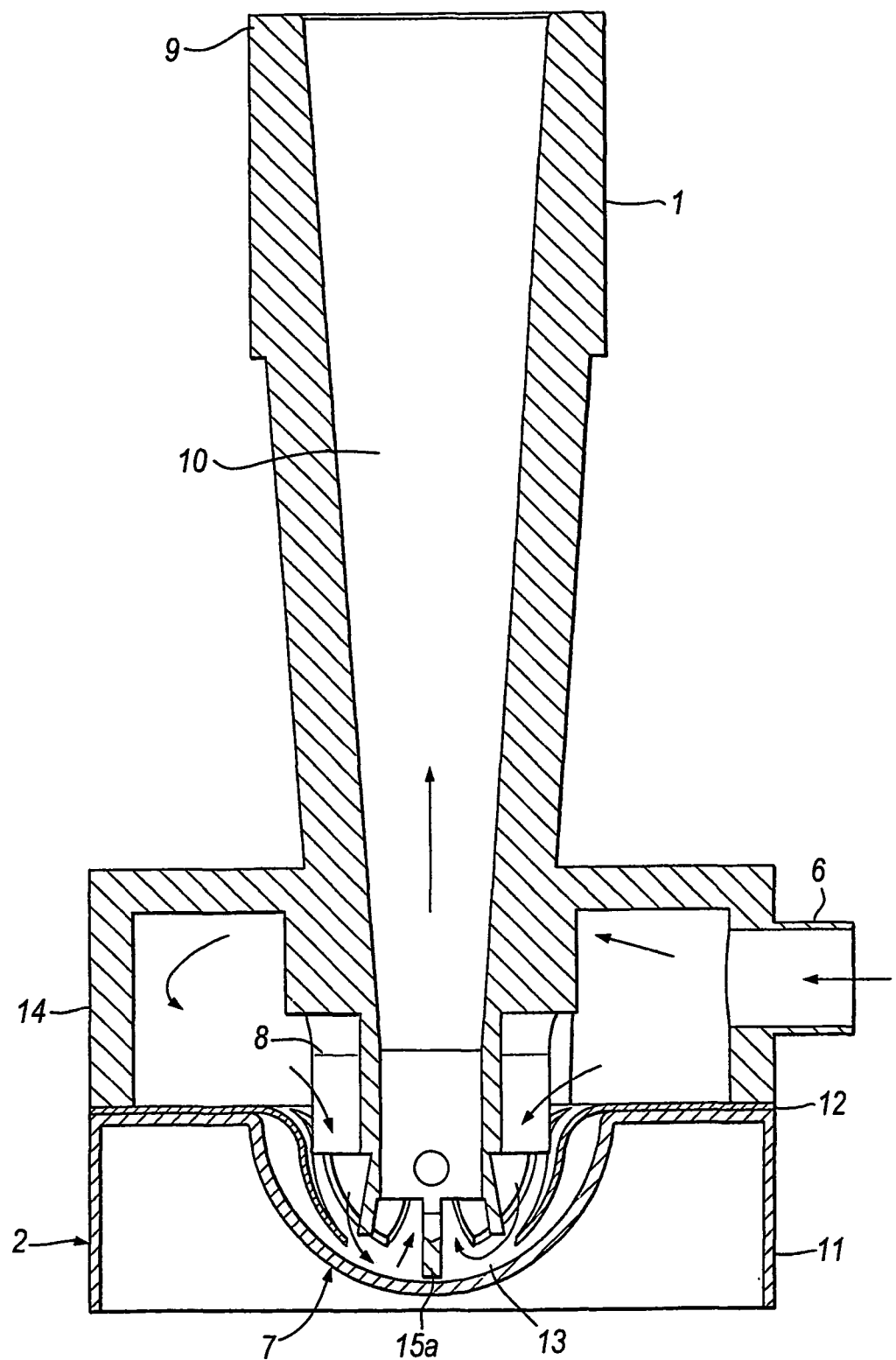
FIG. 3 is a sectional view through the suction tube and blister pack in FIG. 2 after insertion of the suction tube into the blister pack.
Figure 4:
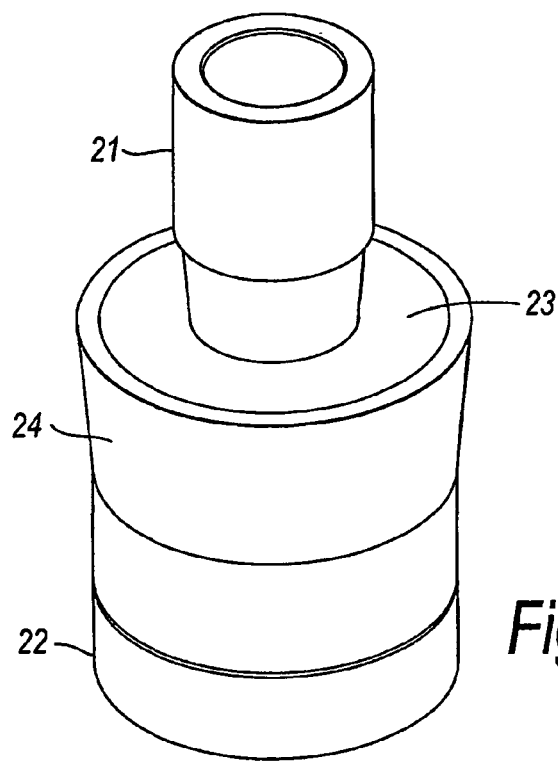
FIG. 4 is a perspective view of a second preferred embodiment of the present invention.
Figure 5:
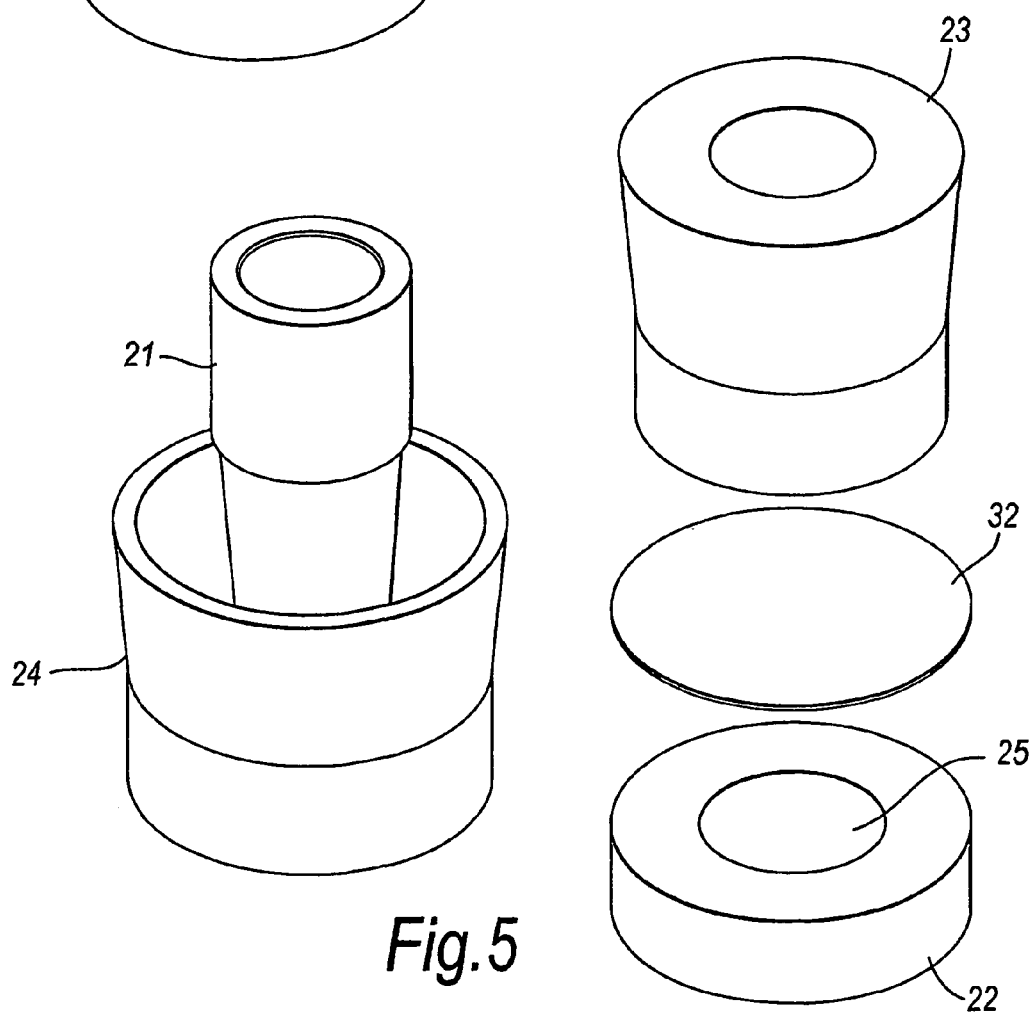
FIG. 5 is an exploded view of the elements in FIG. 4.
Figure 6:
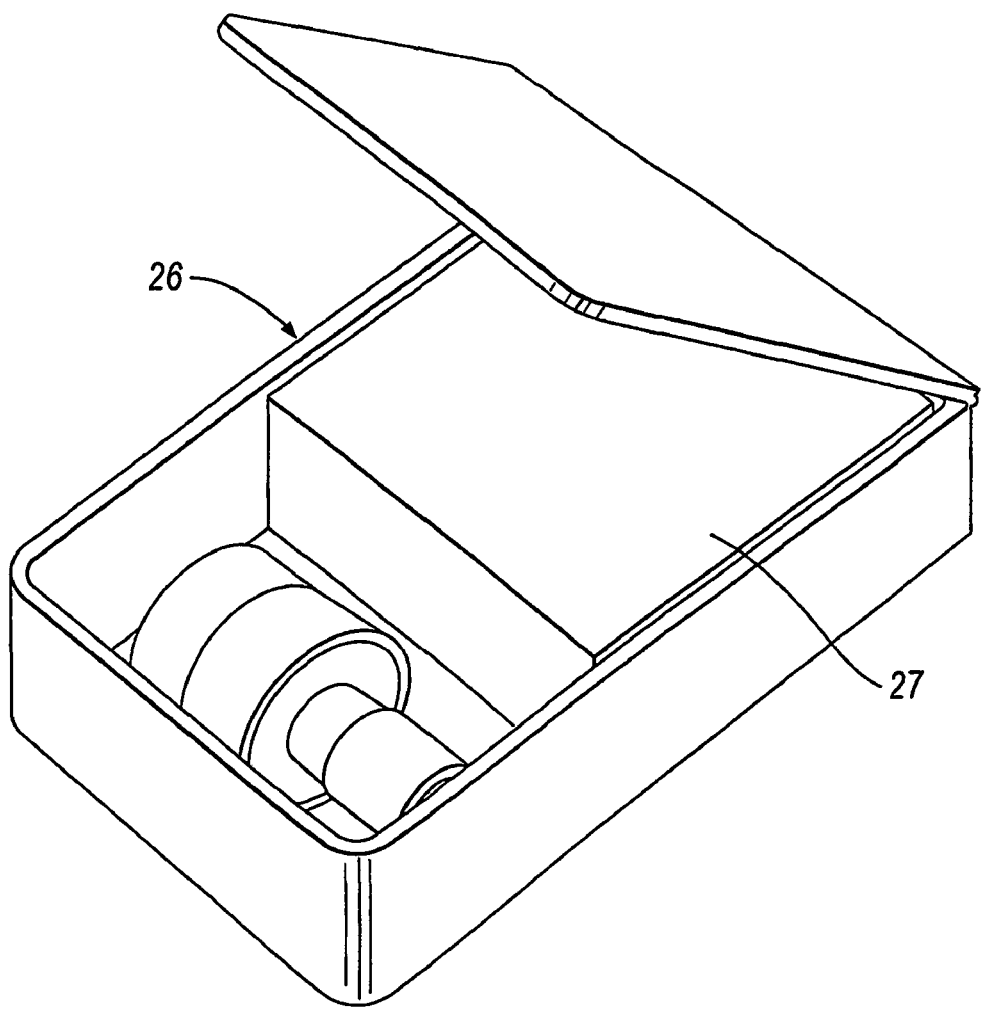
FIG. 6 is a perspective view of the inhalation device in FIG. 4 when placed in a regeneration box.
Figure 7:
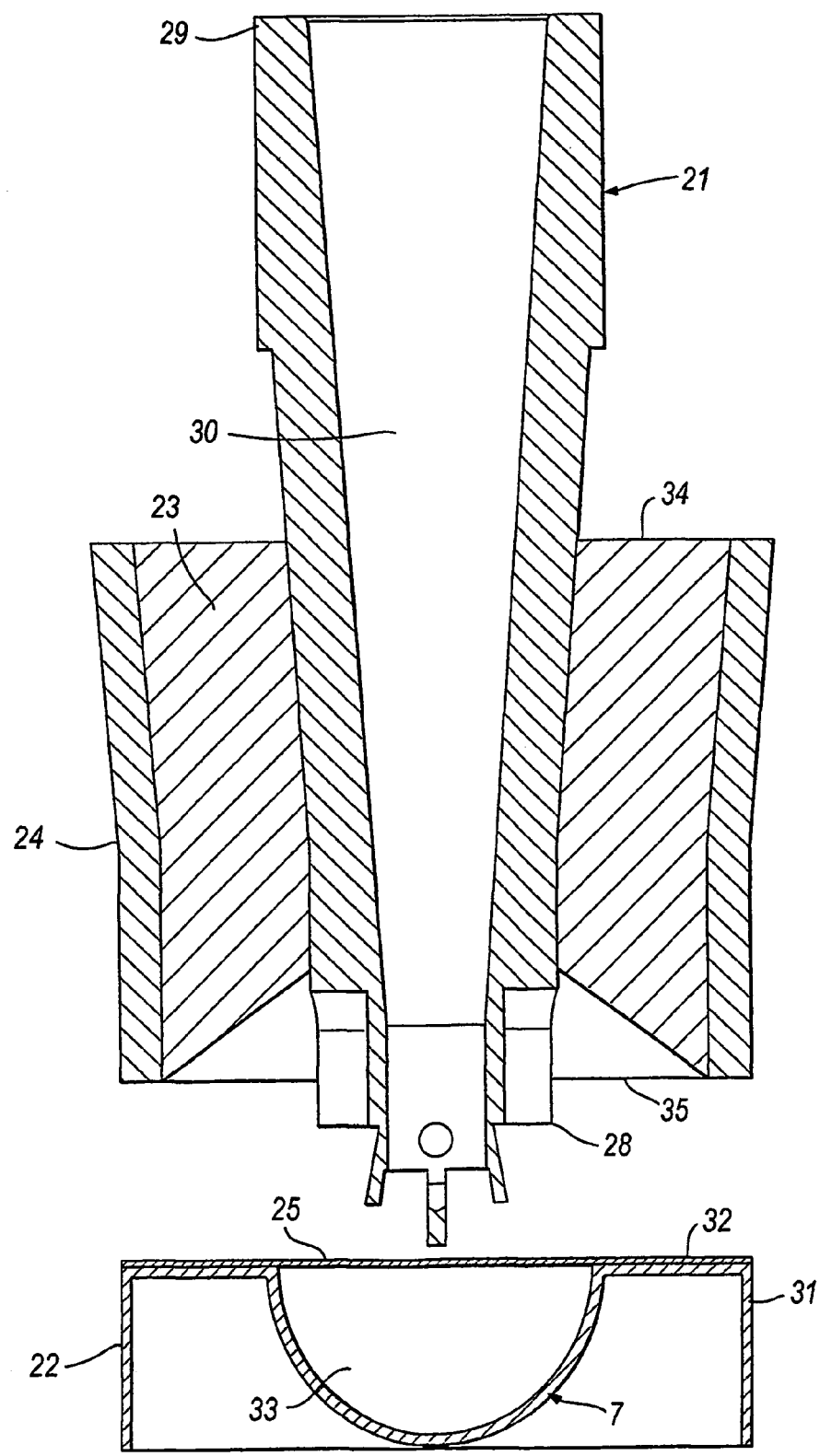
FIG. 7 is a sectional view through the inhalation device in FIG. 4 before insertion of the suction tube into the blister pack.
Figure 8:
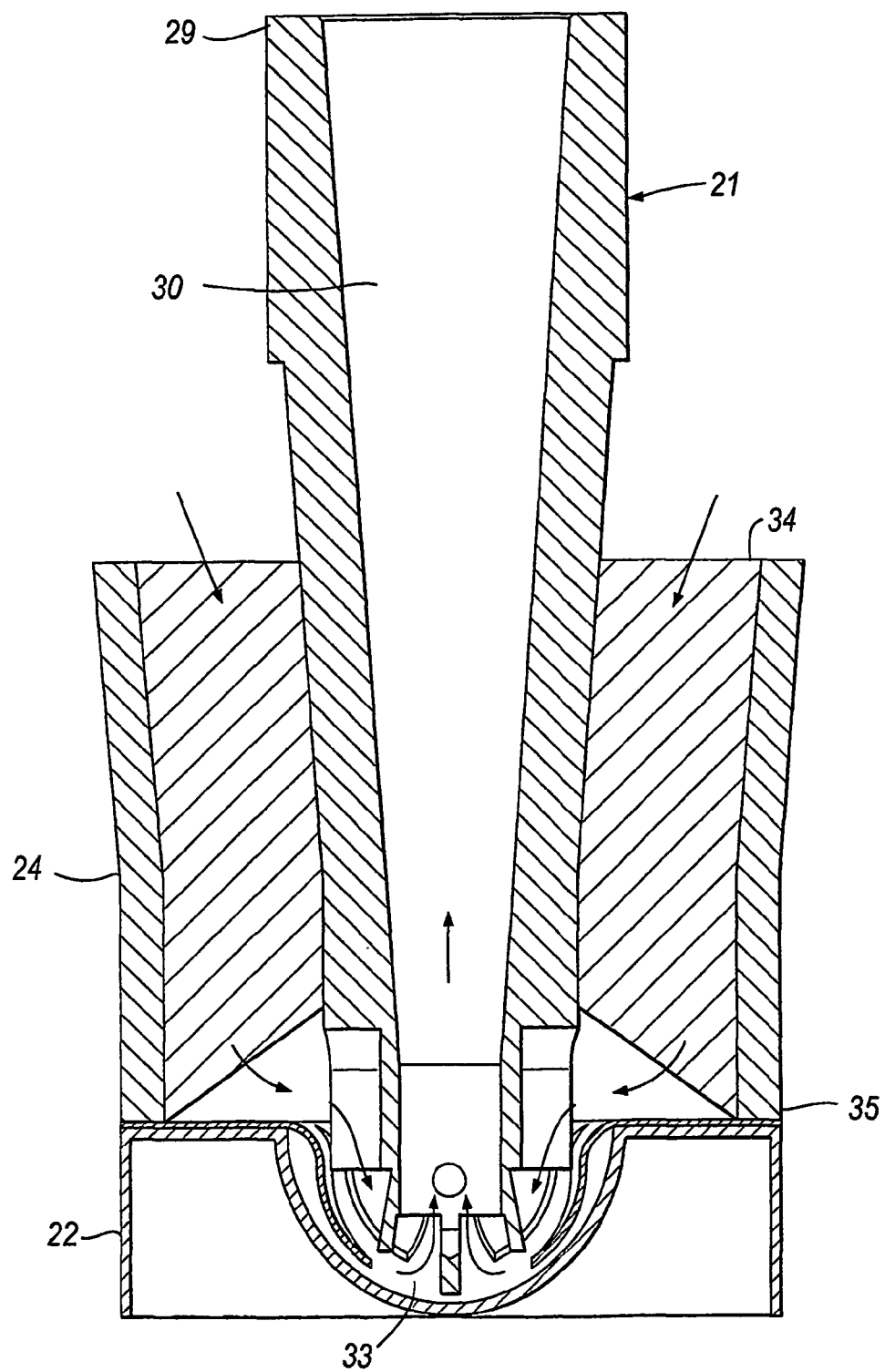
FIG. 8 is a sectional view through the inhalation device in FIG. 4 after insertion of the suction tube into the blister pack.
Figure 11A:
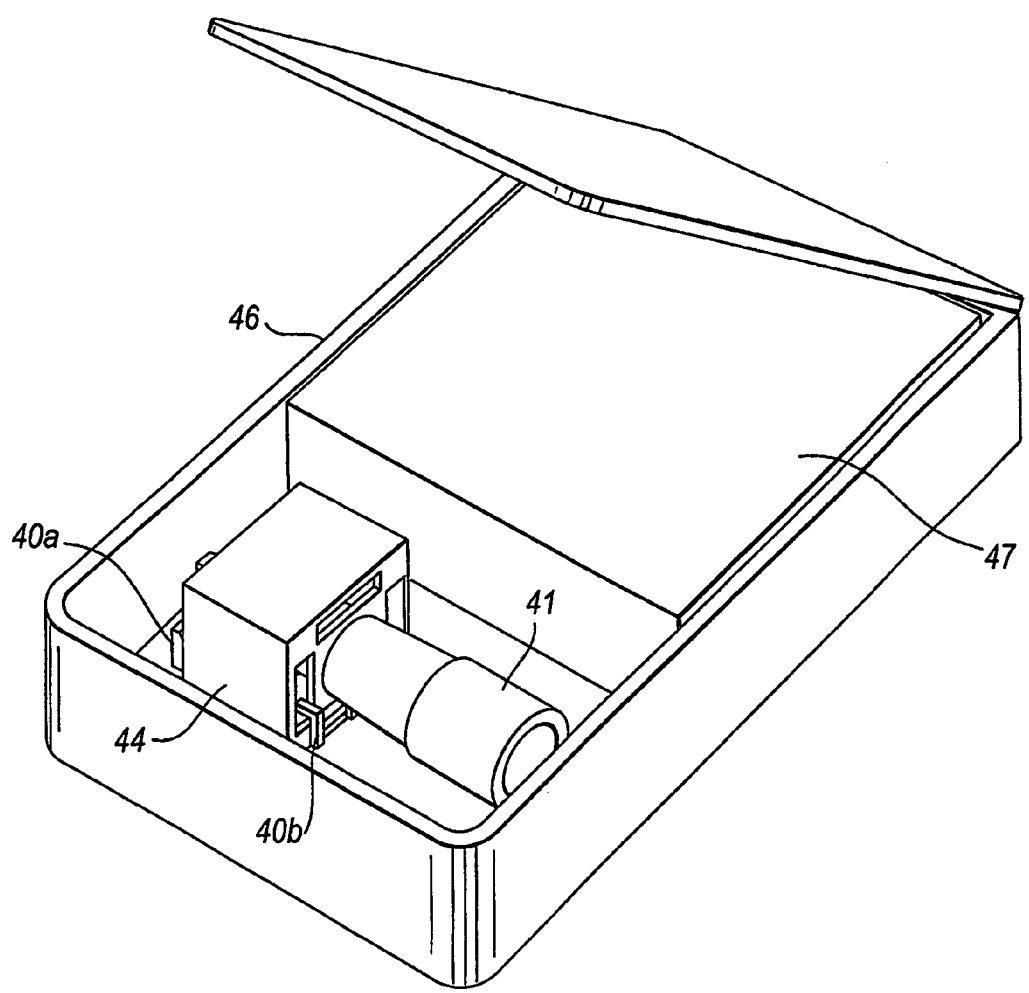
FIG. 11a is a perspective view of the inhalation device in FIG. 9 when placed in a regeneration box.
Figure 11B:
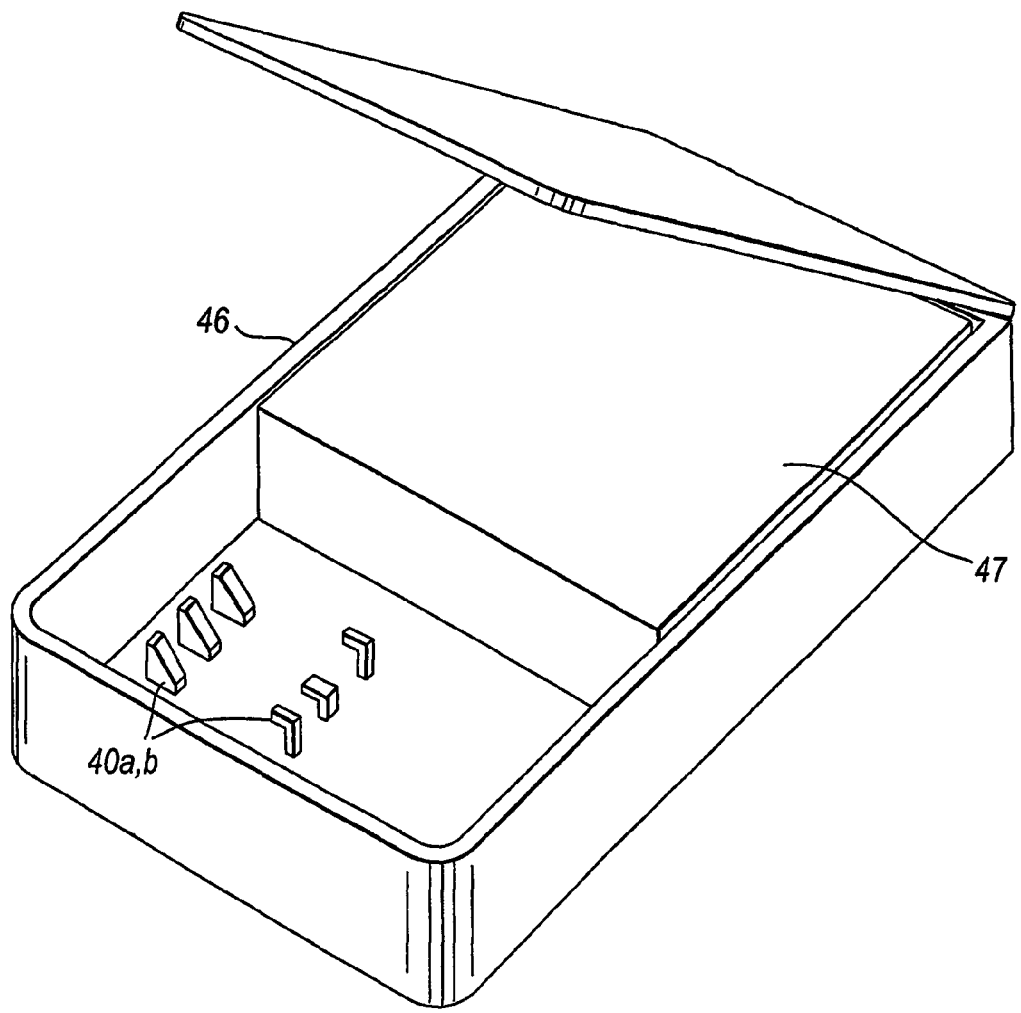
FIG. 11b is a perspective view of the regeneration box in FIG. 11a without the inhalation device.
Figure 12:
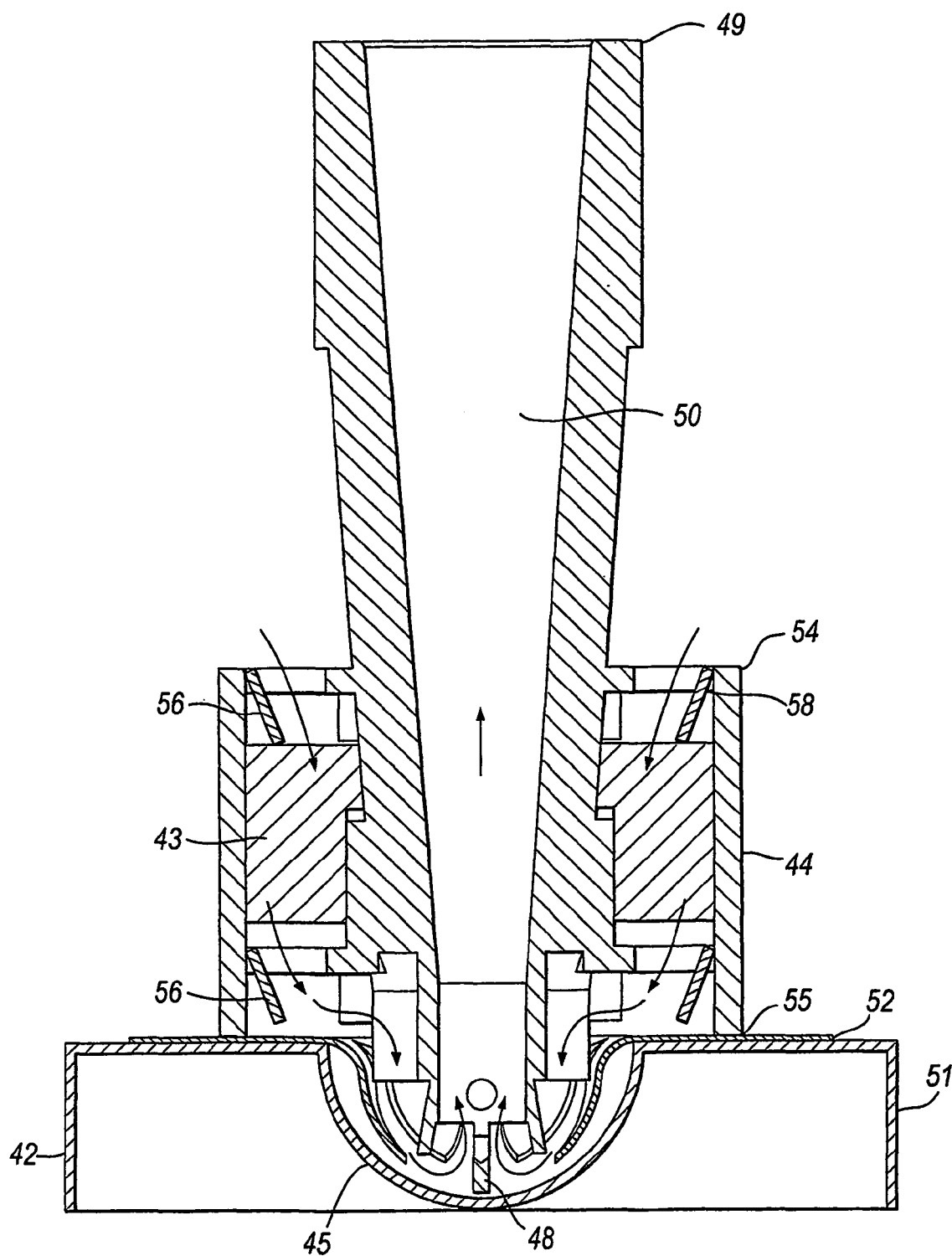
FIG. 12 is a sectional view of the inhalation device in FIG. 9 after insertion of the suction tube into the blister pack.
Figure 13:
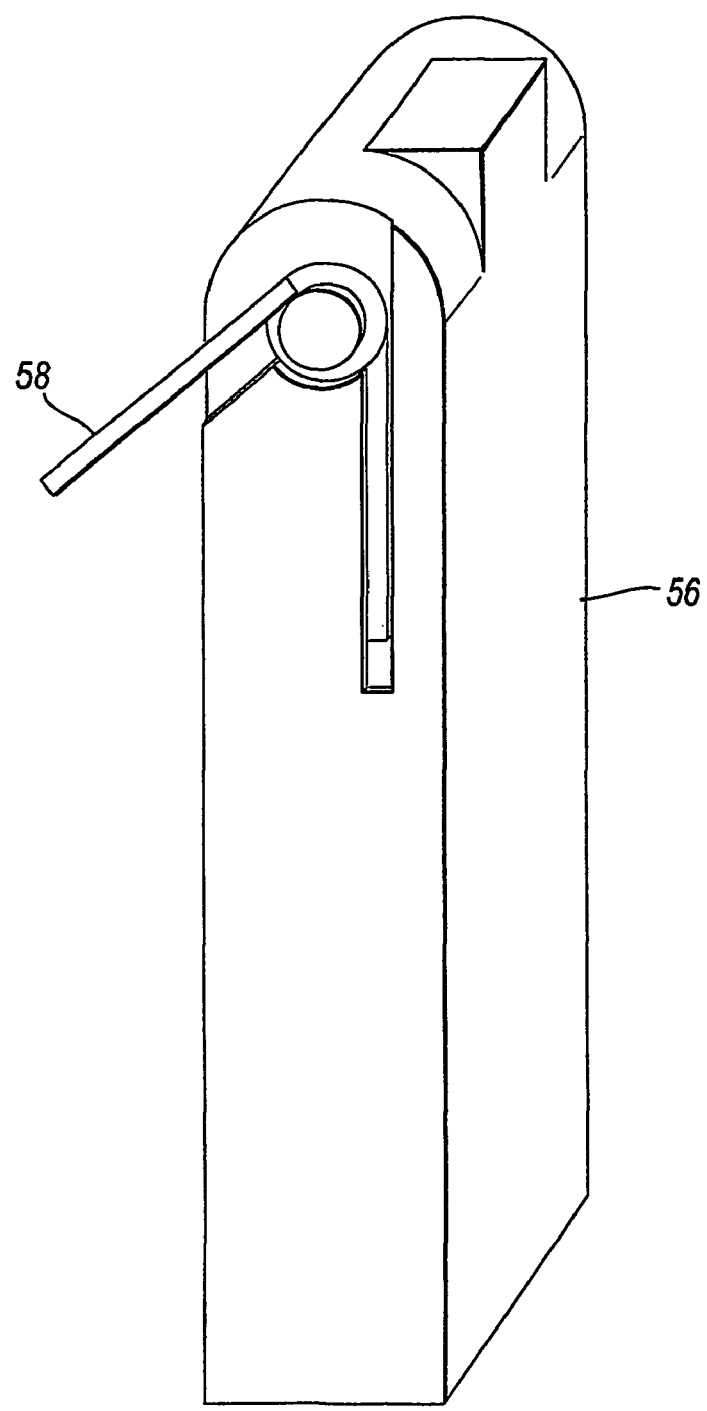
FIG. 13 is an enlarged view of one of the flaps in the inhalation device in FIG. 12.

When the user has penetrated the blister 25 (see FIG. 8) the housing 24 comes to rest on the foil layer 32 above the blister 25 so that when the user inhales, moist air will be drawn through the upper end 34 of the housing 24, down through the drying agent 23 (where it is dried), through the lower end 35 of the housing 24 into the cavity 33 and up through the distal end 28 of the suction tube 21 into the air passageway 30 to the user. The cutting mechanism on the distal end 28 will not be described again in detail since it is substantially identical to that in FIG. 2 and in the further embodiments depicted in FIGS. 9 to 44. Airflow arrows have been added to FIG. 8 to show the direction of airflow.

The drying agent 23 is sufficient for at least one or two inhalations. Although the drying agent 23 is exposed to air at the upper end 34, non-flowing air will be dried slowly so that when the inhalation device is not in use exposure to the surrounding air does not affect it noticeably.

When not in use, and to regenerate the drying agent 23, the inhalation device is stored in an air-tight drying box 26 which is partly filled with a bulk drying agent 27. The drying box 26 must be air-tight to avoid undesirable degradation of the bulk drying agent 27. Preferably, there is sufficient bulk drying agent 27 to regenerate the drying agent 23 enough times to empty all the blisters 25 in the blister pack 22.

A third preferred embodiment of the present invention is depicted in FIGS. 9 to 13. The inhalation device comprises a suction tube 41 and a blister pack 42. A drying agent 43 surrounds the suction tube 41 and is held within a housing 44. This embodiment works in a similar manner to that depicted in FIGS. 4 to 8 except that the housing 44 is provided with hinged flaps 56 biased into a closed (horizontal) position by weak springs 58. The flaps 56 are located at both the upper end 54 and the lower end 55 of the housing 44. When the user inhales the flaps 56 will be opened and moist air will flow into the housing 44 as indicated by the airflow arrows in FIG. 12. The moist air will pass through the drying agent 43, (where it is dried), through the flaps 56 at the lower end 55 of the housing 44 and into the cavity 53. The dried air will then lift the powder formulation within the blister 45 in the blister pack 42 up through the distal end 48 of the suction tube 41 and through air passage 50 to the mouthpiece 49. Reference numerals 51 and 52 identify the lower base and the upper foil respectively of the blister pack 42.

The flaps 56 are open during the entire inhalation procedure by the pressure difference created on suction by the user. As soon as inhalation ceases, the weak spring force will return the flaps 56 to the closed (horizontal) position. The drying agent 43 has to have a very fast initial moisture adsorption and there must be a slow migration of water within the drying agent once adsorbed. In this way, the initial volume of moist air which enters housing 44 will be dried but the drying surface will saturate very quickly. At this point, no further moisture can be adsorbed. However, after use the adsorbed water will eventually reach equilibrium in the drying agent and the drying surface will once again be able to adsorb moisture. Accordingly, a drying box may not be required because the drying agent 43 naturally regenerates after each use and has sufficient capacity to adsorb the moisture involved in emptying a complete blister pack 42. However, if further drying is required, the drying box 46 in FIGS. 11*a* and 11*b* could be used. The flaps 56 open on contact with three sets of hooks 40*a*, 40*b* when the inhalation device is returned to the drying box 46 to regenerate the drying agent 43. Each hook set 40*a*, 40*b* comprises a sloped guide 40*a* and a hook element 40*b*. The hook elements 40*b* can open three of the flaps 56 which is sufficient to ensure that the drying agent 43 is adequately exposed to the bulk drying agent 47. In a similar manner to the second embodiment, there should be sufficient bulk drying agent 27 to allow the user to empty a complete blister pack 42. The advantages of this embodiment over the second embodiment are that the flaps 56 protect the drying agent 43 when removed from the drying box 46 and that the airflow can be shut off after a specified time or a specified volume of airflow, e.g. using servo motors. Clearly, the less exposure the drying agent 43 has to moist air when removed from the drying box 46 before inhalation, the less risk there is of the drying agent 43 performing inadequately during inhalation.

Figure 15:
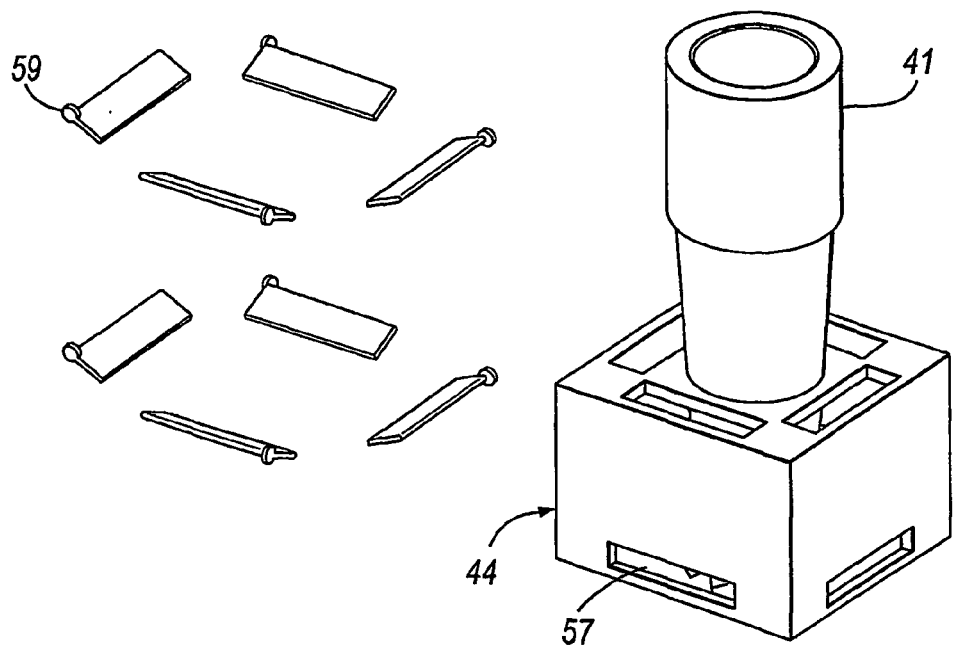
FIG. 15 is an exploded view of the elements in FIG. 14.
Figure 14:
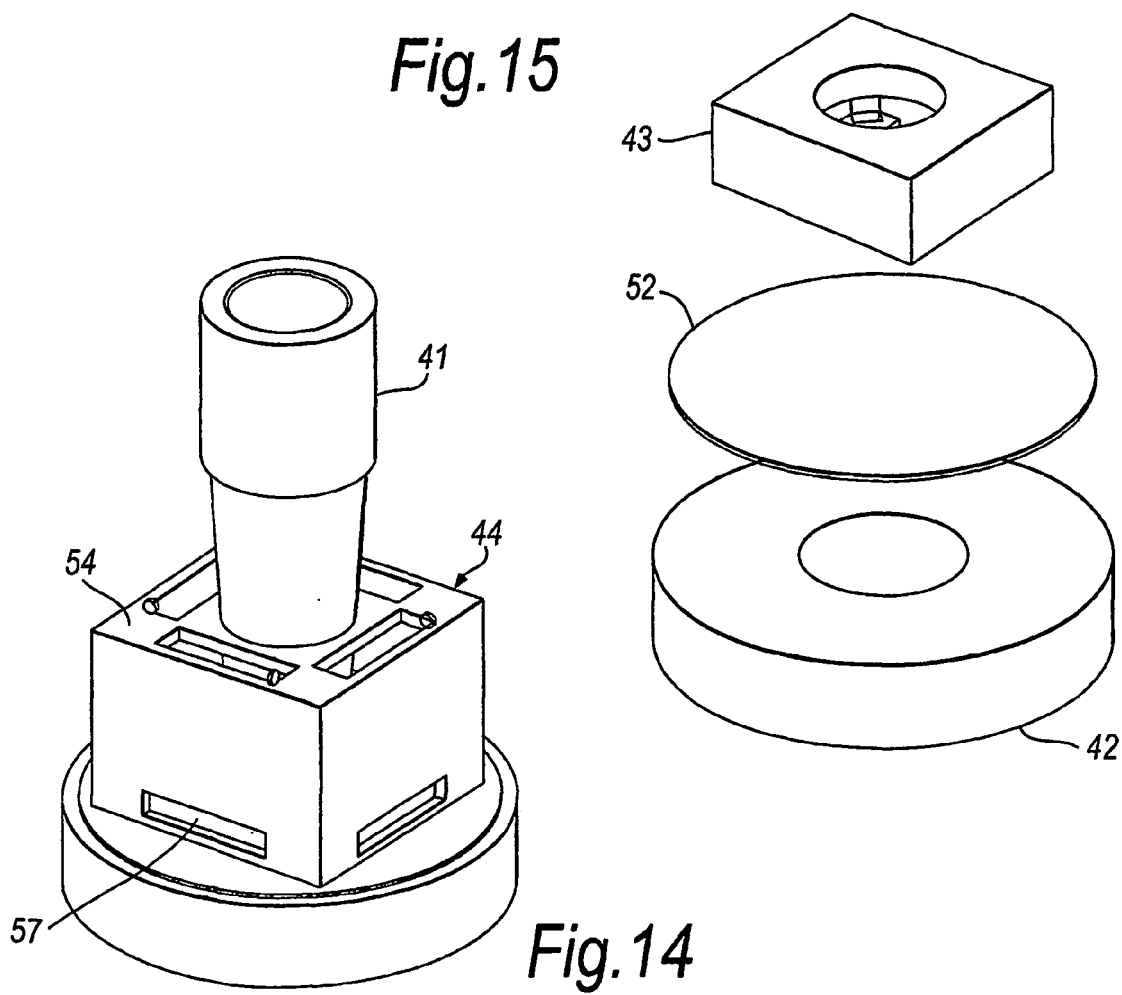
FIG. 14 is a perspective view of a fourth preferred embodiment of the present invention.
Figure 16:
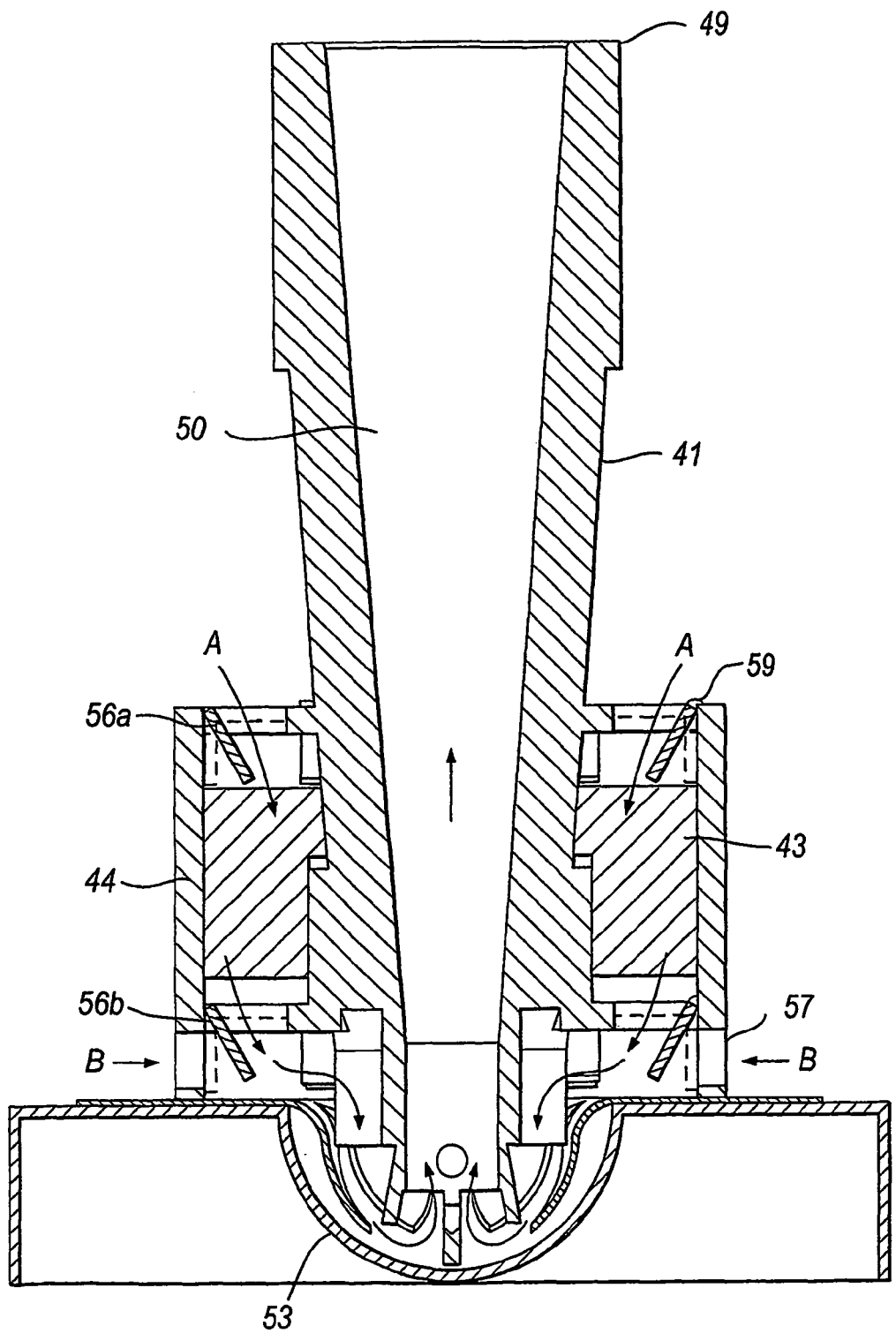
FIG. 16 is a sectional view of the inhalation device in FIG. 14 after insertion of the suction tube into the blister pack.
Figure 19:
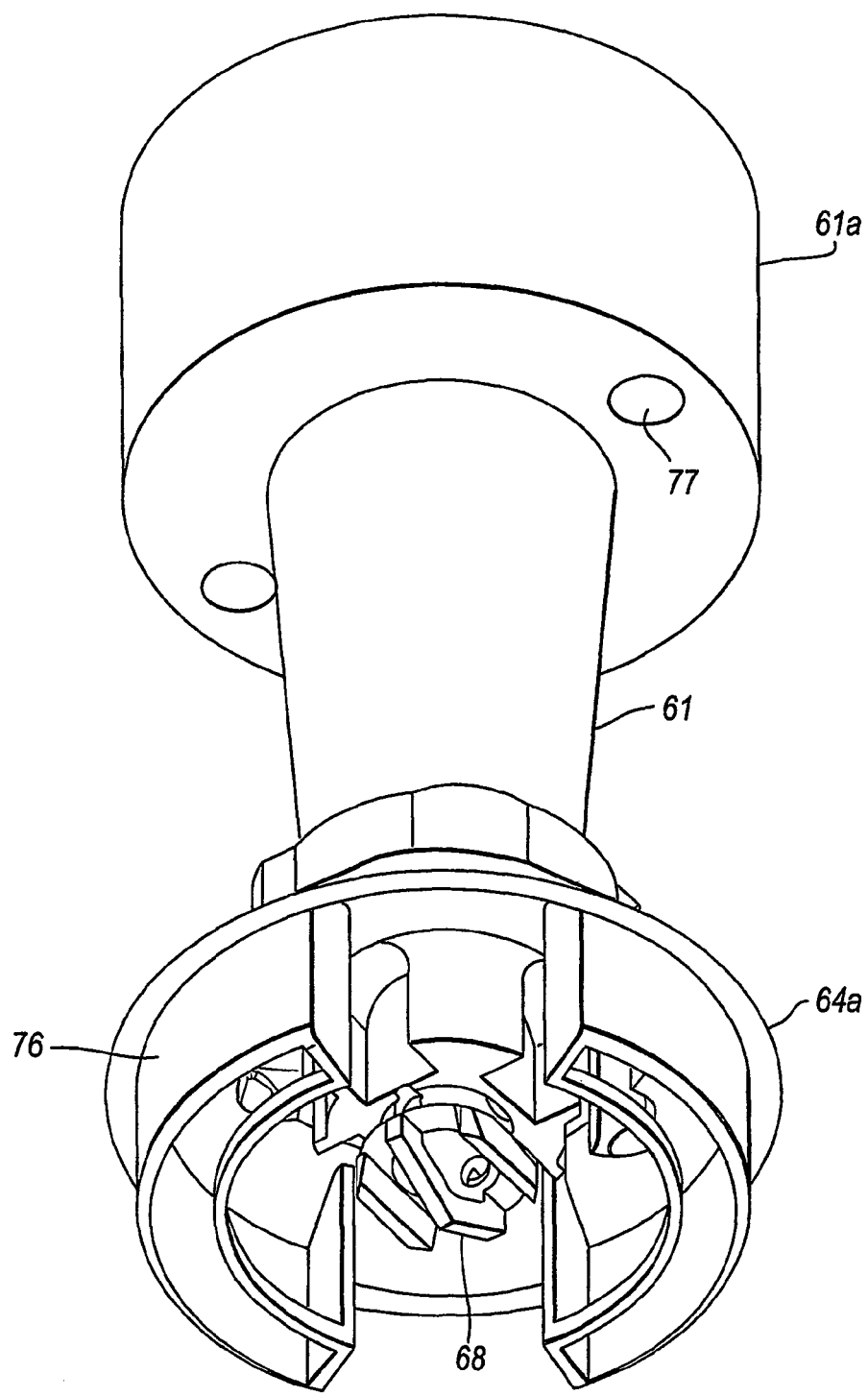
FIG. 19 is a perspective view from below of the suction tube in FIG. 18.
Figure 20:
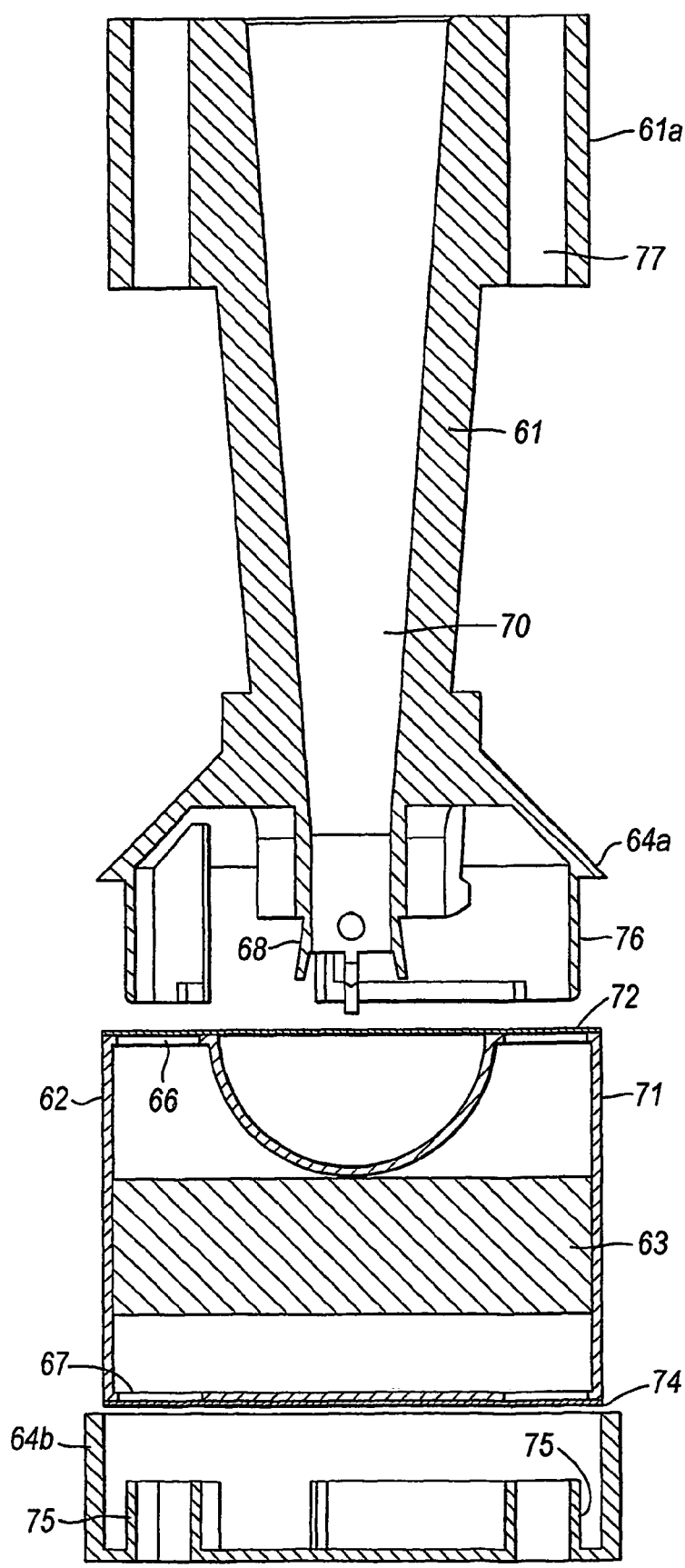
FIG. 20 is a sectional view through the inhalation device in FIG. 17 before insertion of the suction tube into the blister pack.

A fourth preferred embodiment of the inhalation device described with reference to FIGS. 14 to 16 is provided with bypass inlets 57 at the lower end 55 of the housing 44. In all other respects, the inhalation device in FIGS. 14 to 16 is identical to the third embodiment depicted in FIGS. 9 to 13. In this embodiment, the flaps 56*a* and 56*b* are constructed to allow an airflow of approximately 0.1 to 0.2 liters and then close automatically. In this example, the flaps 56*a* and 56*b* are operated by servo motors 59 and the closing point can be time dependent or dependent on the volume of airflow. During the initial airflow (indicated by airflow arrows A in FIG. 16) the bypass inlets 57 will be closed by flaps 56*b*, i.e. flaps 56*a* and 56*b* will be in the vertical position shown so that there will be no airflow B. When the flaps 56*a* and 56*b* close (i.e. they sit in a substantially horizontal position), air will then flow through the bypass inlets 57 (indicated by airflow arrows B in FIG. 16). Typically, the flaps 56 will be set to close and shut off airflow A when the volume of air which has been inhaled through the suction tube 41 is sufficient to remove the entire contents of a cavity 53. At this point, the air which is inhaled no longer needs to be dried and accordingly, the air can enter the housing 44 via the bypass inlets 57. An advantage of the third and fourth embodiments over the embodiments depicted in FIGS. 1 to 8 is that the volume of drying agent 43 can be reduced since less drying is needed if the flaps 56 close automatically.

A fifth preferred embodiment is depicted in FIGS. 17 to 21 and differs from the previous embodiments in that the drying agent is located in the blister pack. The inhalation device comprises a suction tube 61 and a blister pack 62 with a drying agent 63 located inside the blister pack 62. The housing for directing air to the air inlet at the distal end 68 of the suction tube 61 comprises a skirt 64*a* extending downwardly at the distal end 68 of the suction tube 61 and a blister pack holder 64*b* in which the blister pack 62 sits.

In this embodiment, the suction tube 61 has an enlarged mouthpiece 69 in the form of a collar 61*a* through which bypass channels 77 are formed. The purpose of the bypass channels 77 is to ease the effort required by the user to inhale. Clearly, some air will enter the bypass channels 77 rather than through the blister pack holder 64*b*. Often, it is the initial airflow which determines the quality of the inhalation of the powdered medicament.

The blister pack 62 comprises one or more blisters 65, each of which will be provided with a separate block of drying agent 63. The blister pack 62 comprises a lower base 71 and an upper foil layer 72. The lower base 71 holds one or more cavities 73 and also forms an enclosure around the drying agent 63. The lower base 71 is provided with upper annular channels 66 and lower annular channels 67 which help to direct the airflow through the blister pack 62. A lower foil layer 74 seals the blister pack 62 until the inhalation device is ready for use.

Figure 21:
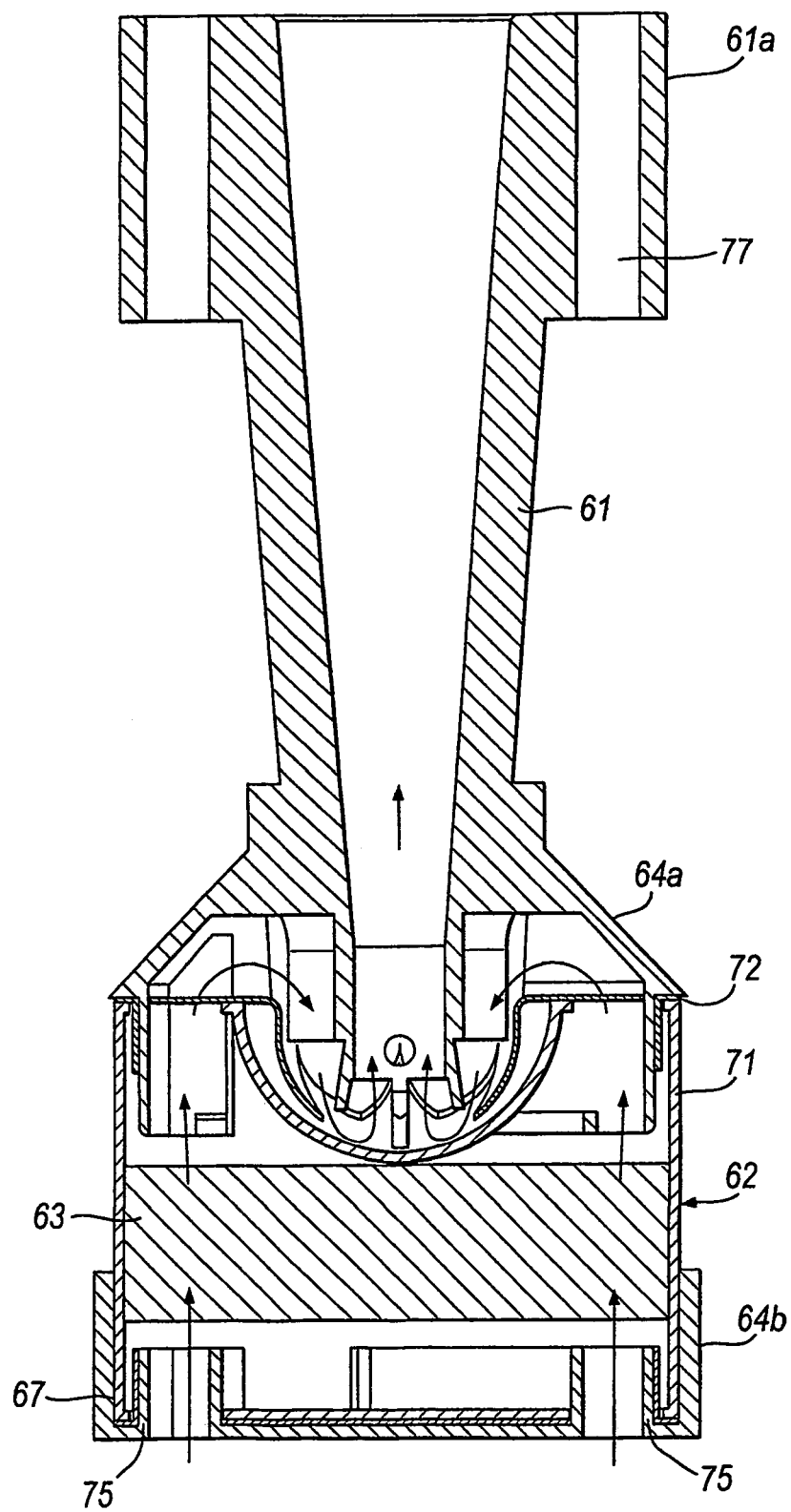
FIG. 21 is a sectional view through the inhalation device in FIG. 17 after insertion of the suction tube into the blister pack.
Figure 24:
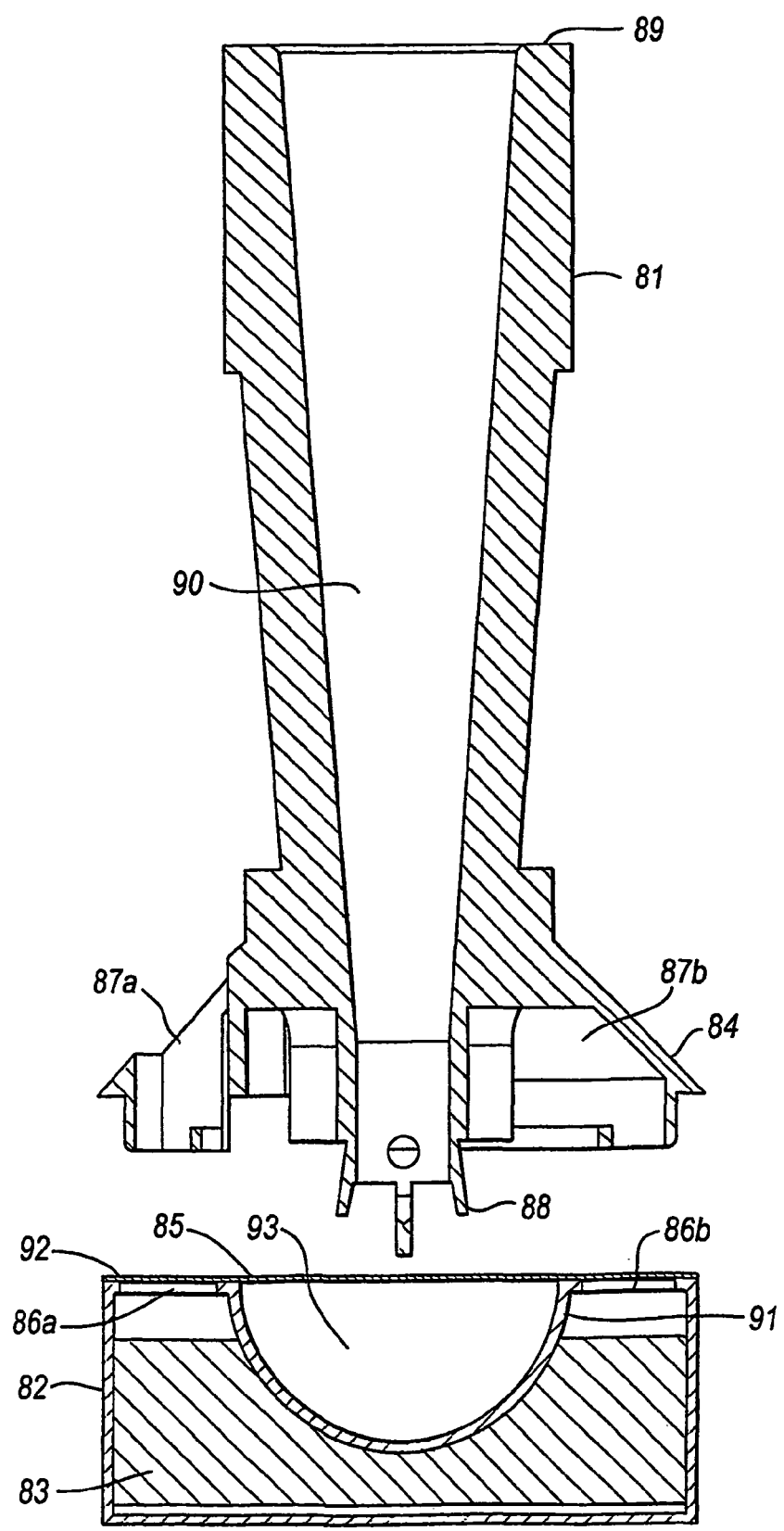
FIG. 24 is a sectional view through the inhalation device in FIG. 22 before insertion of the suction tube into the blister pack.
Figure 25:
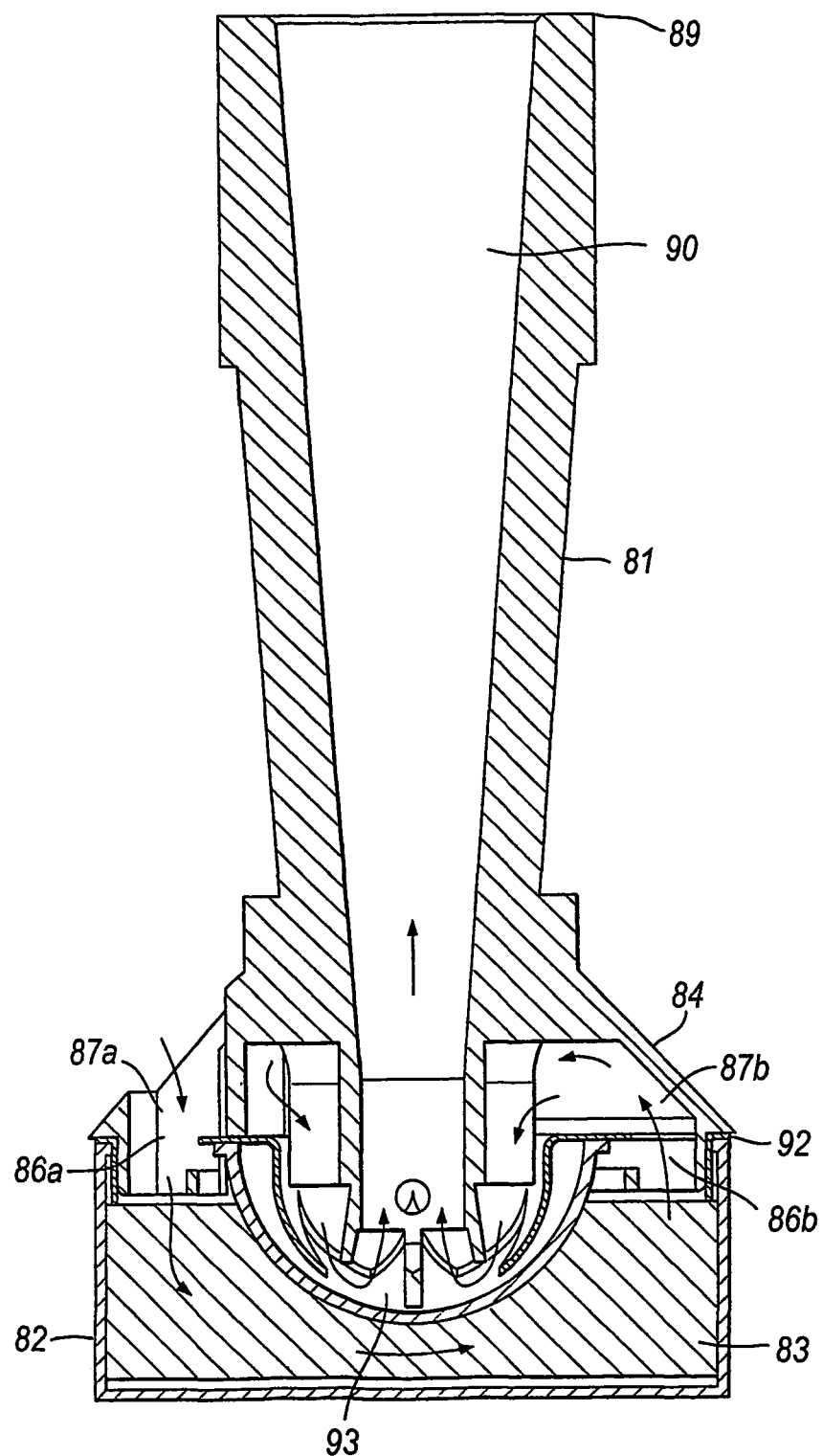
FIG. 25 is a sectional view through the inhalation device in FIG. 22 after insertion of the suction tube into the blister pack.

In use, the blister pack 62 is first pushed into the blister pack holder 64*b*. At this point lower foil layer 74 is broken by the upstanding walls 75 which sit in annular channels 67 and form the entrance for air into the blister pack 62. The suction tube 61 should then be pushed into the blister pack 62 by breaking the upper foil layer 72. At the end of the skirt 64a are depending walls 76 which will sit inside the annular channels 66. Reference should now be made to FIG. 21 which includes airflow arrows showing how moist air is drawn in through the blister pack holder 64b, up through the drying agent 63, where drying occurs, and then into annular channels 66 before entering the interior volume of skirt 64a and subsequently being drawn into cavity 73, up through the air inlet 68 of the suction tube 61, into air passage 70 and to the mouthpiece 69.

FIGS. 22 to 26 depict a sixth preferred embodiment which is similar to the sixth embodiment in that the drying agent is also located in the blister pack. However, the airflow enters the blister pack from above rather than from below. The inhalation device comprises a suction tube 81 and a blister pack 82 which holds the drying agent 83. The drying agent 83 is in the form of a block which is shaped to sit below a cavity 93 in the blister pack 82. The blister pack 82 is provided with two part-annular channels 86a and 86b which help to direct the airflow through the blister pack 82. The suction tube 81 has a distal end 88 which forms the air inlet and a proximal end 89 which forms the air outlet or mouthpiece. The distal end 88 of the suction tube 81 includes a skirt 84 which acts as a housing for directing air to the air inlet. The skirt 84 includes a part-annular inlet channel 87a which will sit inside annual channel 86a when the suction tube 81 is pushed into the blister pack 82.

The blister pack 82 comprises one or more blisters 85, each of which will be provided with a separate block of drying agent 83. The blister pack has a lower base 91 and an upper foil layer 92. The lower base 91 holds one or more cavities 93 and also forms an enclosure for drying agent 83.

Figure 26:
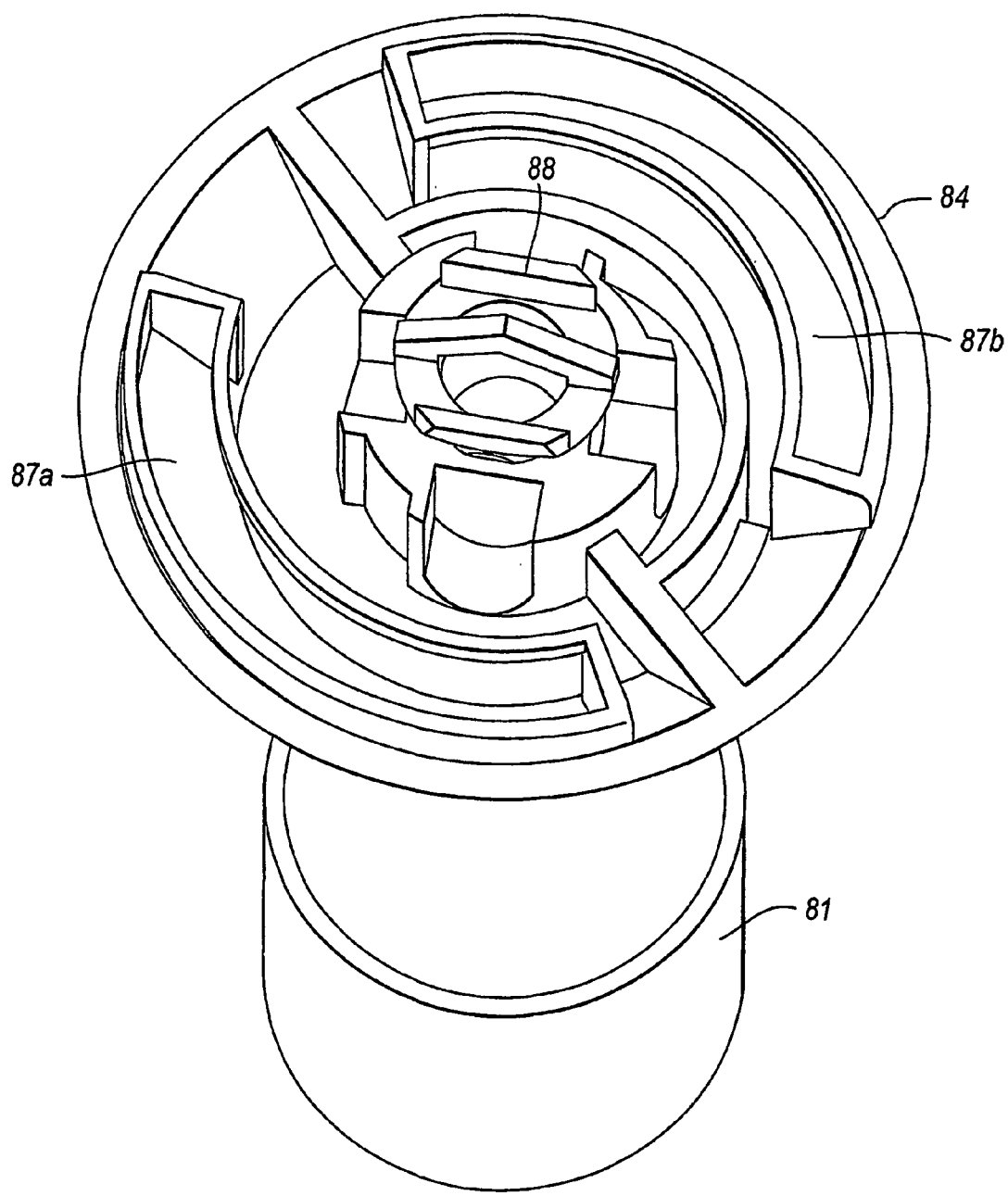
FIG. 26 is a perspective view from below of the suction tube in FIG. 22.
Figure 29:
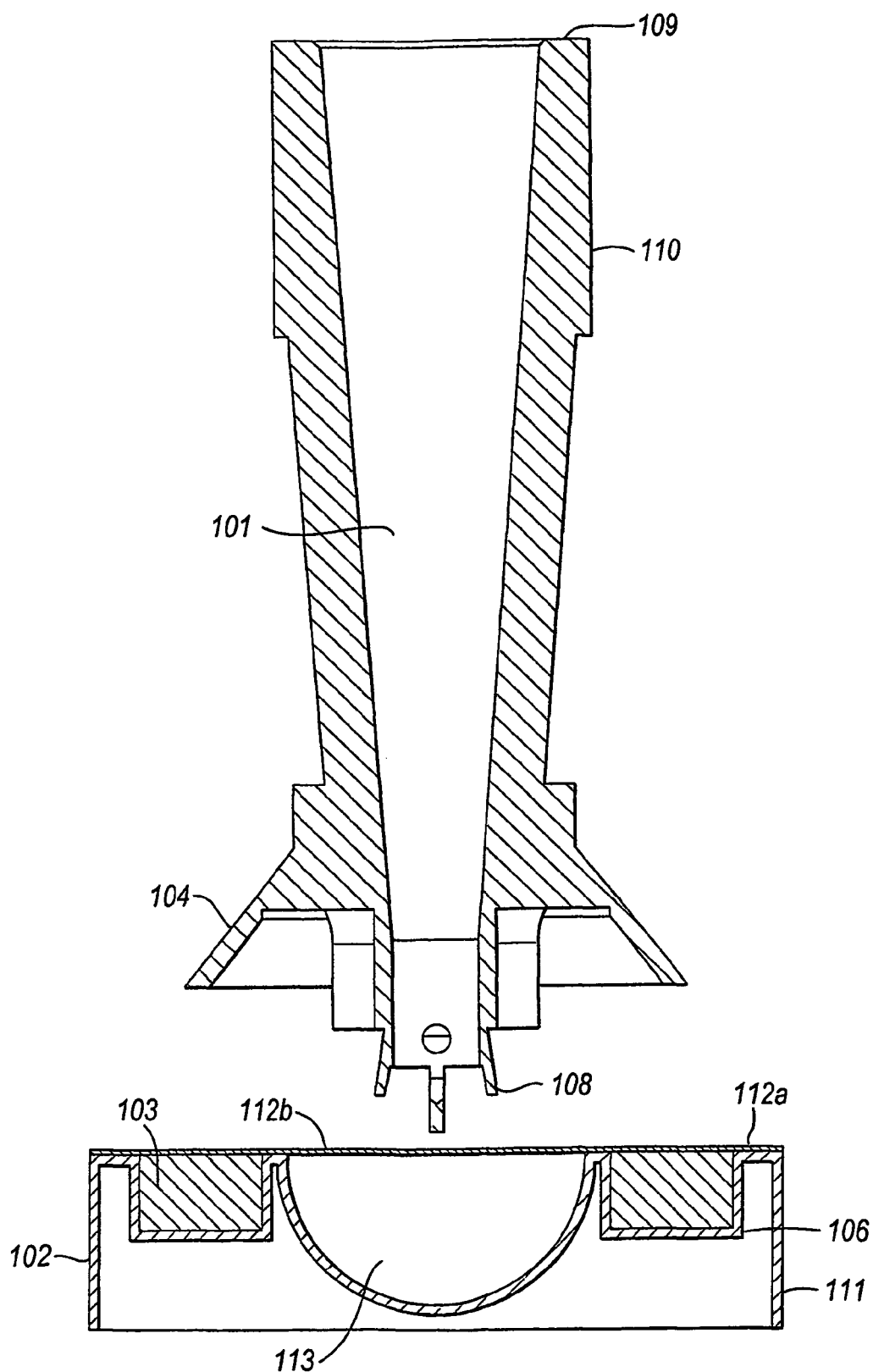
FIG. 29 is a sectional view through the inhalation device in FIG. 27 before insertion of the suction tube into the blister pack.

In use, the user will push the suction tube 81 into the blister pack 82 and the distal end 88 will penetrate the foil layer 92. When the user inhales, moist air will be drawn into annular channel 87a (see FIG. 25 with airflow arrows). The air will then pass into the blister pack 82 through annular channel 86a and into the drying agent 83. The air will be dried as it passes through the drying agent 83, eventually re-entering the volume 87b within skirt 84 of the suction tube 81. The air then passes down through the broken foil layer 92 and into cavity 93 lifting the powder formulation up into air passage 90 and to the mouthpiece 89. FIG. 26 is a view from below of the suction tube 81, depicting the annular channel 87a, the volume 87b and the distal end 88 forming the air inlet.

This embodiment is more compact than the fifth embodiment depicted in FIGS. 17 to 21 and will avoid the user covering the air intake with the hands since the hands do not need to touch the skirt 84. In contrast, in FIG. 17, it is clear that the user could inadvertently block the air intake in the blister pack holder 64b. However, the fifth embodiment will permit a larger airflow through the inhalation device.

A seventh embodiment is depicted in FIGS. 27 to 31 in which the drying agent is also located in the blister pack. The inhalation device comprises a suction tube 101 and a blister pack 102 which holds the drying agent 103. The drying agent 103 is in the form of a flexible tube which can be placed in a cavity 106 in the blister pack 102. The tube of drying agent 103 is constructed such that it will sit substantially level with the top surface of the blister pack 102. The suction tube 101 has a distal end 108 which forms the air inlet and a proximal end 109 which forms the air outlet or mouthpiece. At the distal end 108 the suction tube 101 has a skirt. 104 which acts as a housing to direct air to the air inlet 108.

The blister pack 102 comprises one or more blisters 105 each of which is provided with a separate block of drying agent 103. The blister pack 102 has a lower base 111 and an upper foil layer 112a/112b. The lower base 111 holds one or more cavities 113 and also forms an enclosure for the drying agent 103 in the form of cavity 106.

Figure 30:
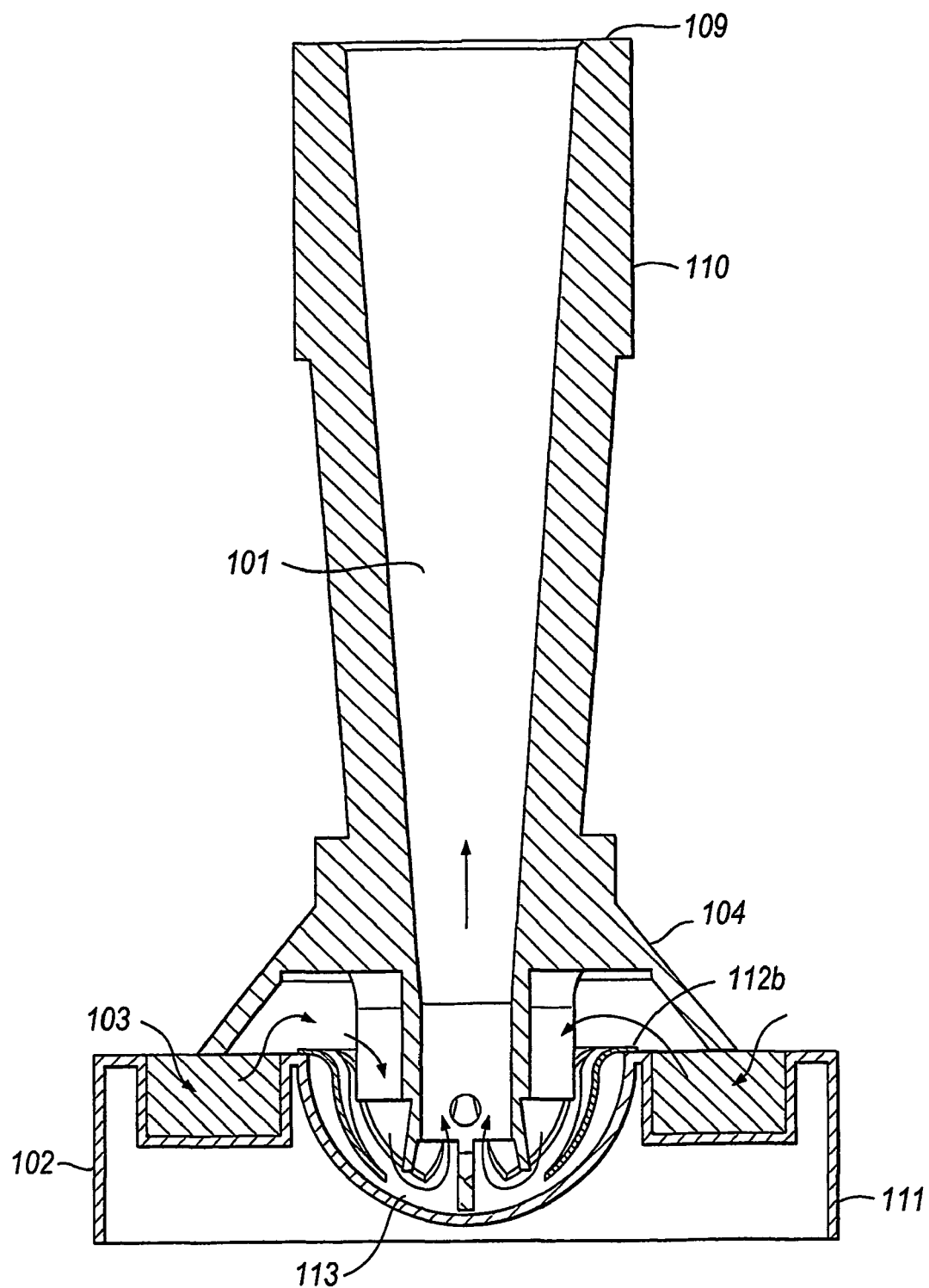
FIG. 30 is a sectional view through the inhalation device in FIG. 27 after insertion of the suction tube into the blister pack.
Figure 31:
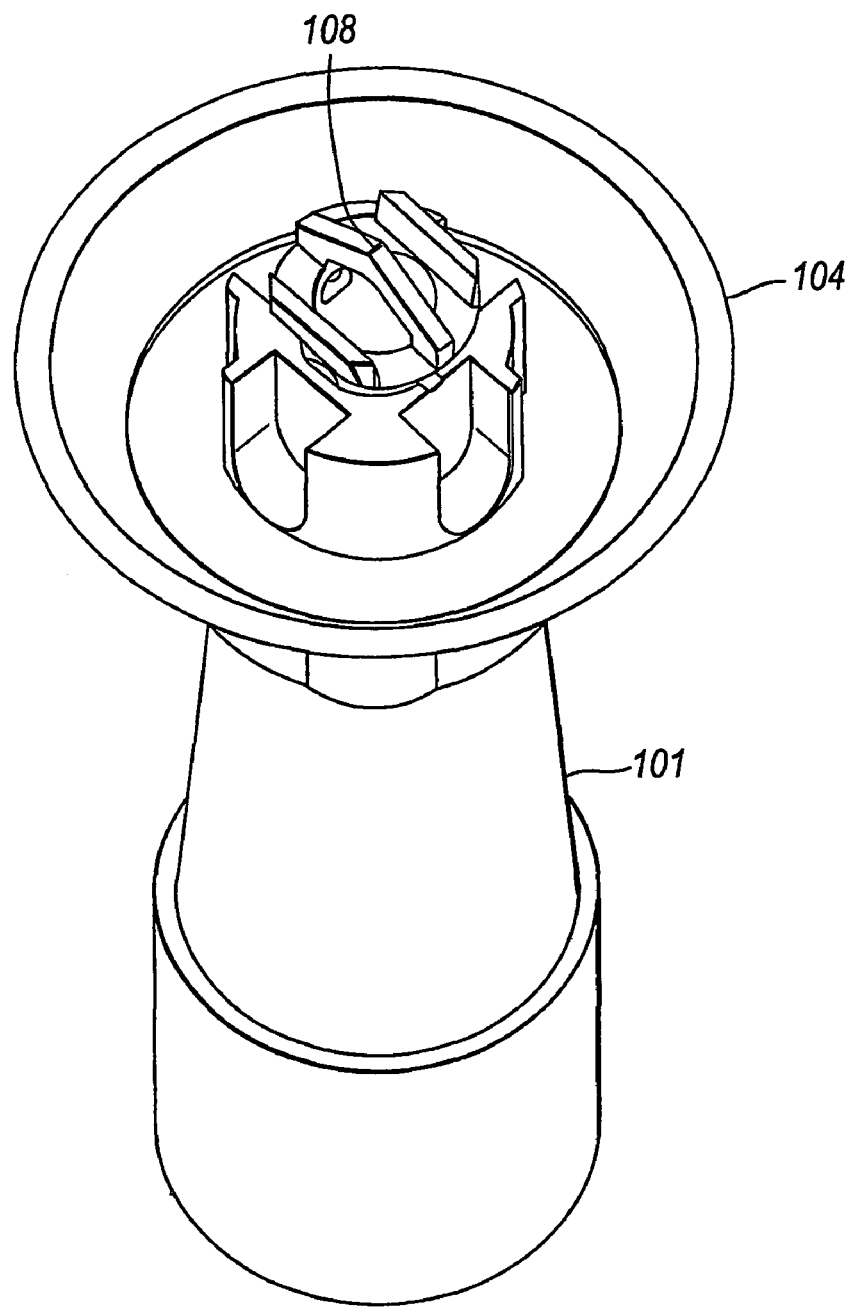
FIG. 31 is a perspective view from below of the suction tube in FIG. 27.
Figure 34:
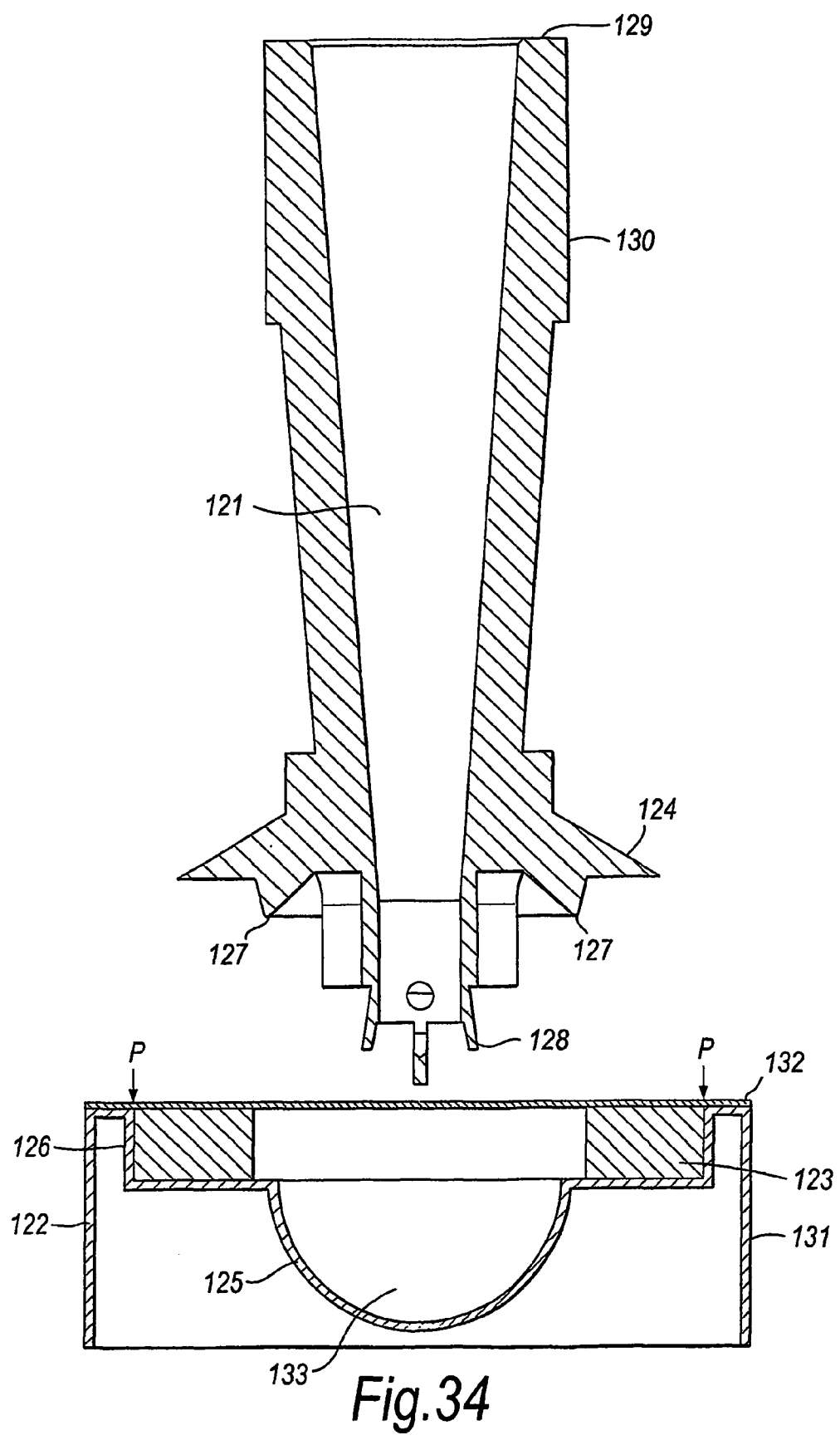
FIG. 34 is a sectional view through the inhalation device in FIG. 32 before insertion of the suction tube into the blister pack.
Figure 35:
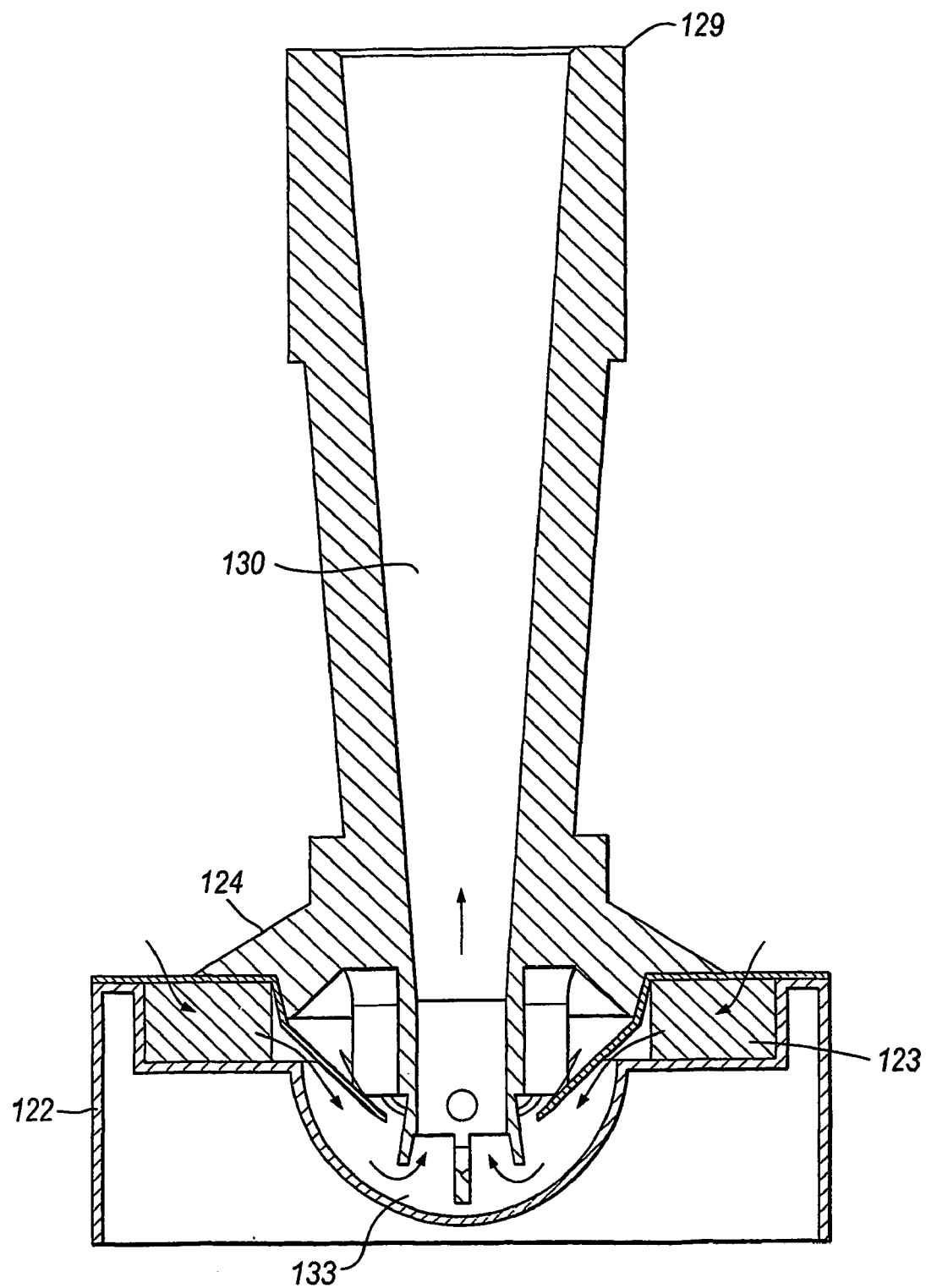
FIG. 35 is sectional view through the inhalation device in FIG. 32 after insertion of the suction tube into the blister pack.
Figures 36, 37:
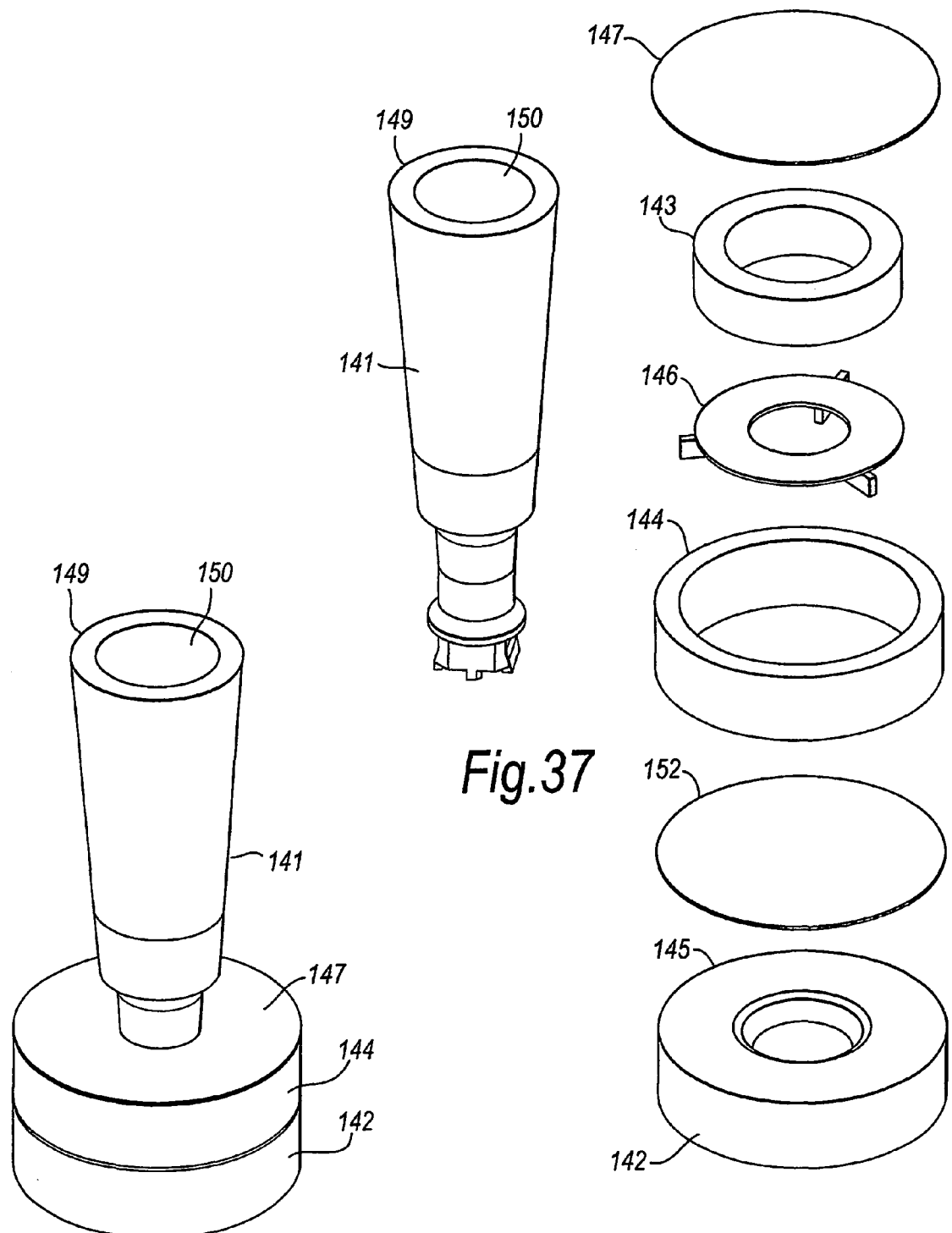
FIG. 36 is a perspective view of a ninth preferred embodiment of the present invention.
FIG. 37 is an exploded view of the elements in FIG. 36.
Figure 38:
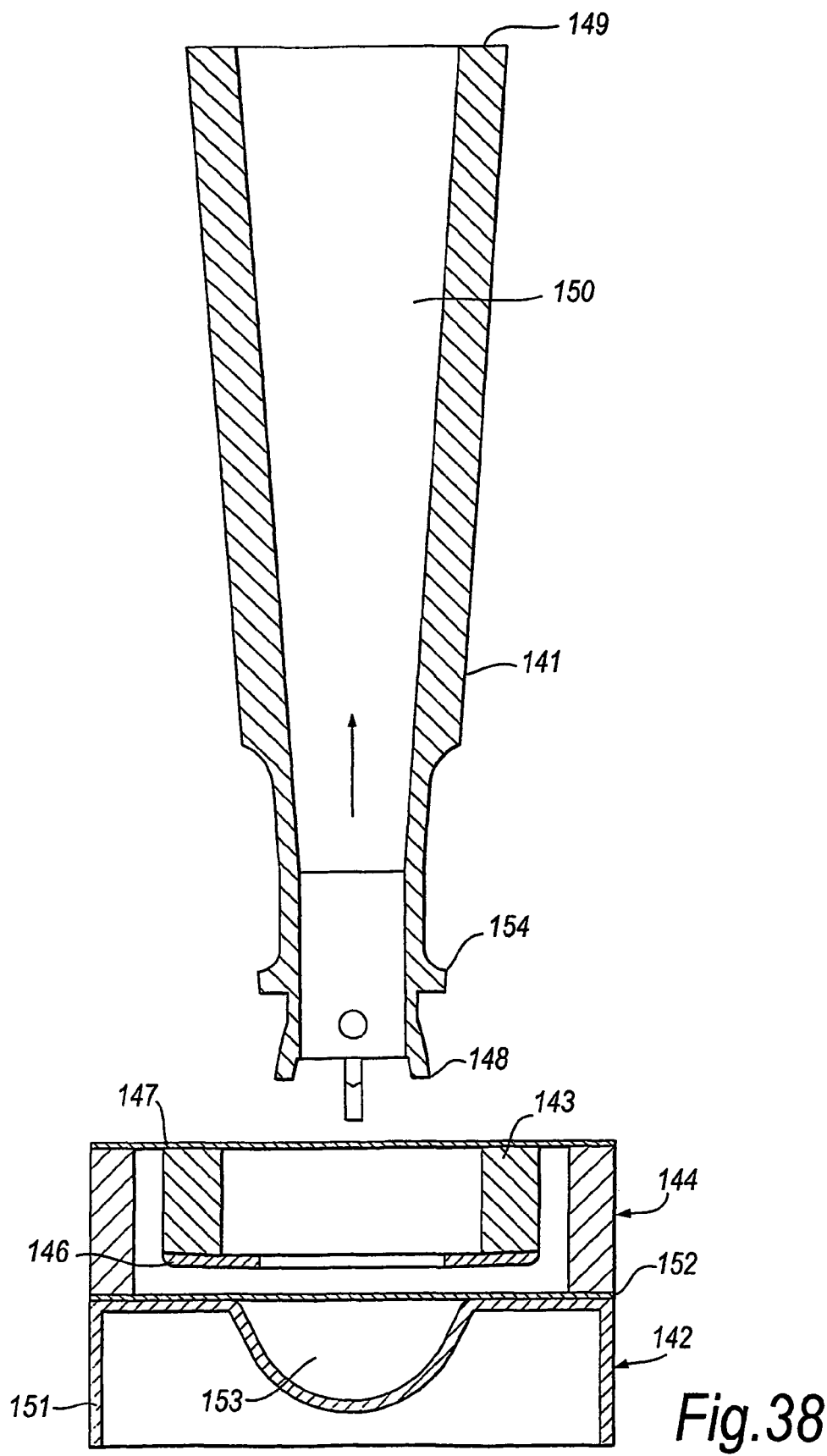
FIG. 38 is a sectional view through the inhalation device in FIG. 36 before insertion of the suction tube into the blister pack.

In use, the user peels off a first annular foil piece 112a and then pushes the suction tube 101 into the blister pack 102. Reference should now be made to FIG. 30 which includes airflow arrows. The penetration of the blister pack 102 by the suction tube 101 pierces a second circular foil piece 112b. The moist air will flow into the cavity 106 which holds the drying agent 103 where it is dried and will then pass up into the volume within the skirt 104 of the suction tube 101. Subsequently, the air will flow down into cavity 113 and up into air passage 110 to the mouthpiece 109.

Alternatively, a single foil layer 112 could be used but a disadvantage with peeling off a single foil layer 112 before penetration of the cavity 113 is that the contents of the cavity 113 and the drying agent 103 would be exposed to moist air even before the suction tube 101 penetrated the cavity 113. Therefore, the arrangement of two foil pieces 112a/112b rather than a single foil layer is preferred. The first foil piece 112a exposes only the drying agent 103 and would be manually removed whereas the second foil piece 112b would be penetrated by the distal end 108 on entering cavity 113. In this way, the powder formulation in cavity 113 would not be affected by moist air.

An eighth preferred embodiment is depicted in FIGS. 32 to 35 which is similar to the seventh embodiment. The aim of this embodiment is to use only a single foil layer which is removed simply by pushing the suction tube 121 into the blister pack 122. The main distinguishing feature are the protrusions 127 which extend below skirt 124 on the suction tube 121. In addition, the cavity 126 in blister pack 122 has been modified such that it sits above the level of the cavity 133 which holds the powder formulation. The drying agent 123 is in a similar tubular form and sits in cavity 126. A single foil layer 132 covers the blister 125 which can be penetrated by the distal end 128 of the suction tube 121. Preferably, the foil layer 132 is perforated at point "P"in the region of the outer radius of the drying agent 123. When the suction tube 121 is pushed into the blister pack 122 the distal end 128 will break the foil 132 but the protrusions 127 will ensure that the foil layer 132 is pushed downwards to clear an airflow passage.

The protrusions 127 will serve to push the foil layer 132 at the Inner diameter of the drying agent 123 which results in tearing of the foil layer 132 at the perforations P near the outer diameter of the drying agent 123. In this way, air will be able to flow into the cavity 126 and through the drying agent 123. Airflow arrows are included in FIG. 35 where it is clear that the air will flow down into the cavity 133 and up through air passage 130 to the mouthpiece 129. In this case, the skirt 124 sits flush against the blister pack 122. Optionally, the cavity 133 could include an additional foil layer to prevent the drying agent 123 from coming into contact with the powder formulation.

The ninth embodiment of the present invention is depicted in FIGS. 36 to 39 and is a variation on the eighth embodiment with the drying agent located above the blister in the blister pack. The inhalation device comprises a suction tube 141 and a blister pack 142. A housing 144 sits above the blister pack 142 and holds an annular block of drying agent 143. The drying agent 143 is sealed within housing 144 by a foil layer 147. An annular divider 146 is secured to the lower face of the drying agent 143. The blister pack 142 comprises a lower base 151 having one or more cavities 153 and an upper foil layer 152 which seals in the powder formulation within the cavity or cavities 153.

Figure 39:
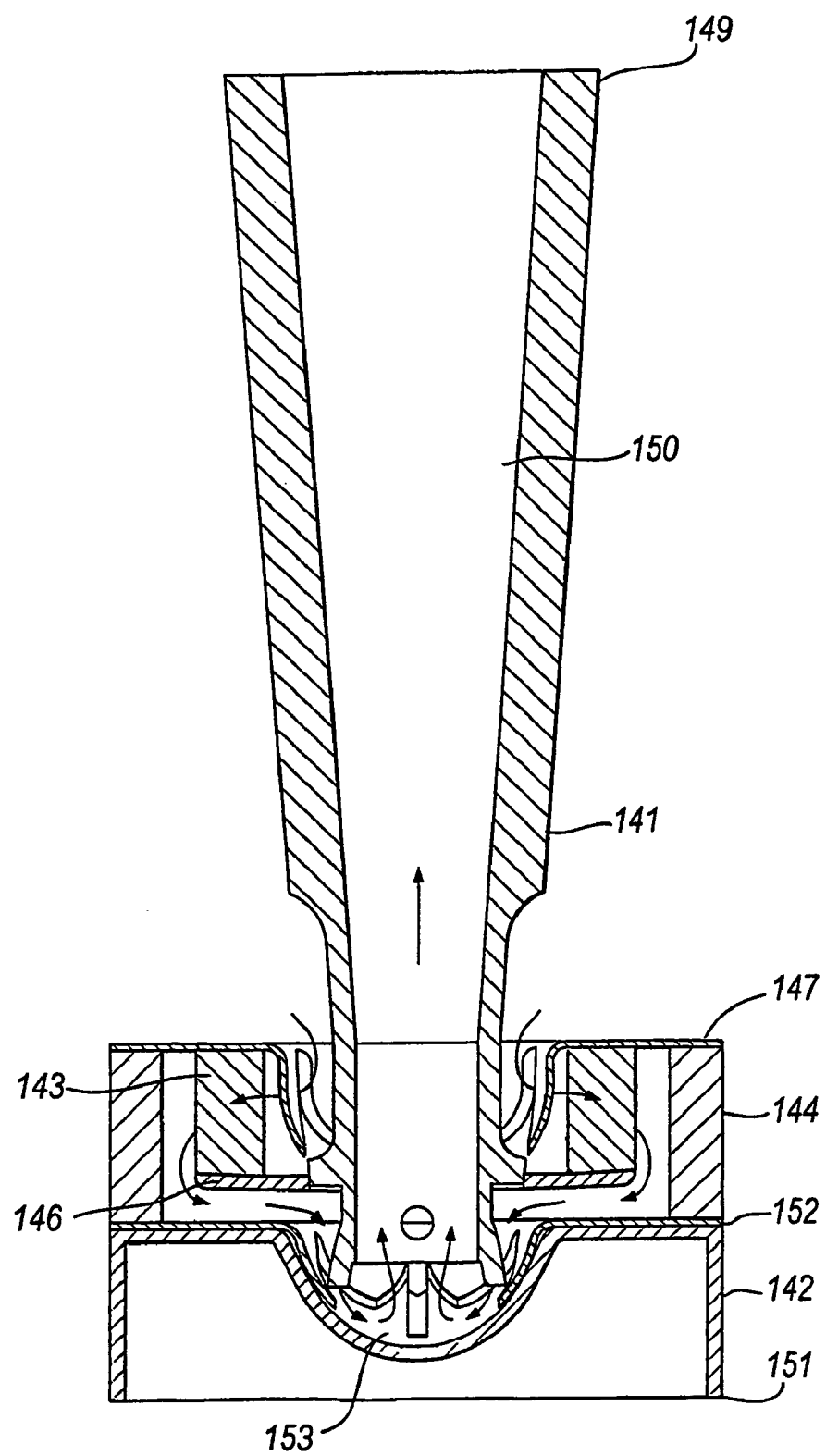
FIG. 39 is a sectional view corresponding to FIG. 38 after insertion into the blister pack.

In use, the distal end 148 of the suction tube 141 is pushed through foil layer 143. The flange 154 on the suction tube 141 will eventually come to rest against the annular divider 146 (see FIG. 39). At this point, the cutting mechanism on the suction tube 141 will have cut the foil layer 152 and penetrated cavity 153. Air will be drawn in as shown in FIG. 39. Since the flange 154 sits tightly against divider 146, air cannot flow directly into the cavity 153 but will have to flow through the drying agent 143. The foil layer 147 protects the drying agent 143 whereas the foil layer 152 protects the contents of the blister 145. In addition, the housing 144 should be virtually impenetrable by moisture in the surrounding air. The foil layer 152 could be made permeable in order to allow the drying agent 143 to keep the powder formulation in the blister 145 dry during storage.

Figure 40:
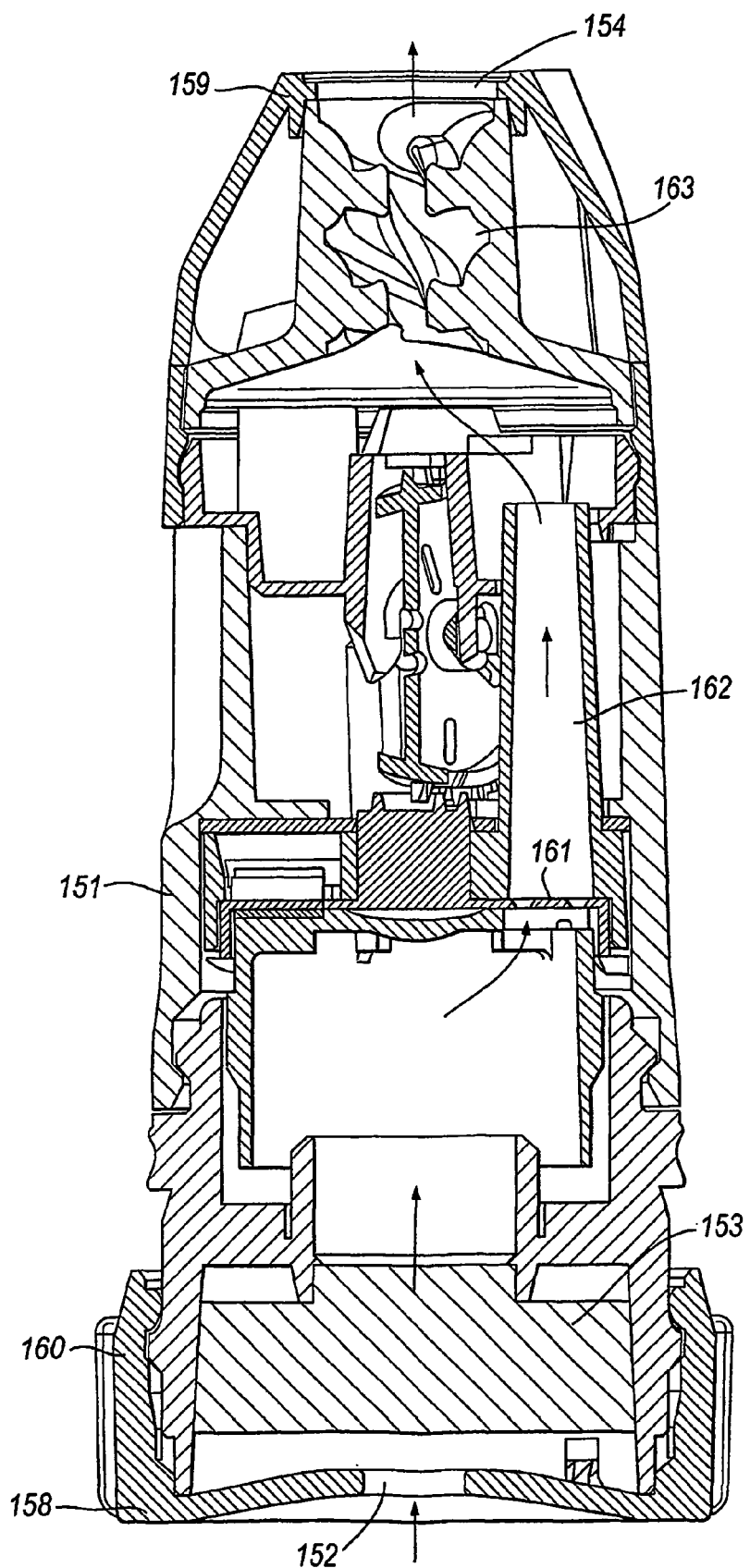
FIG. 40 is a sectional view through a tenth preferred embodiment of the present invention.
Figure 41:
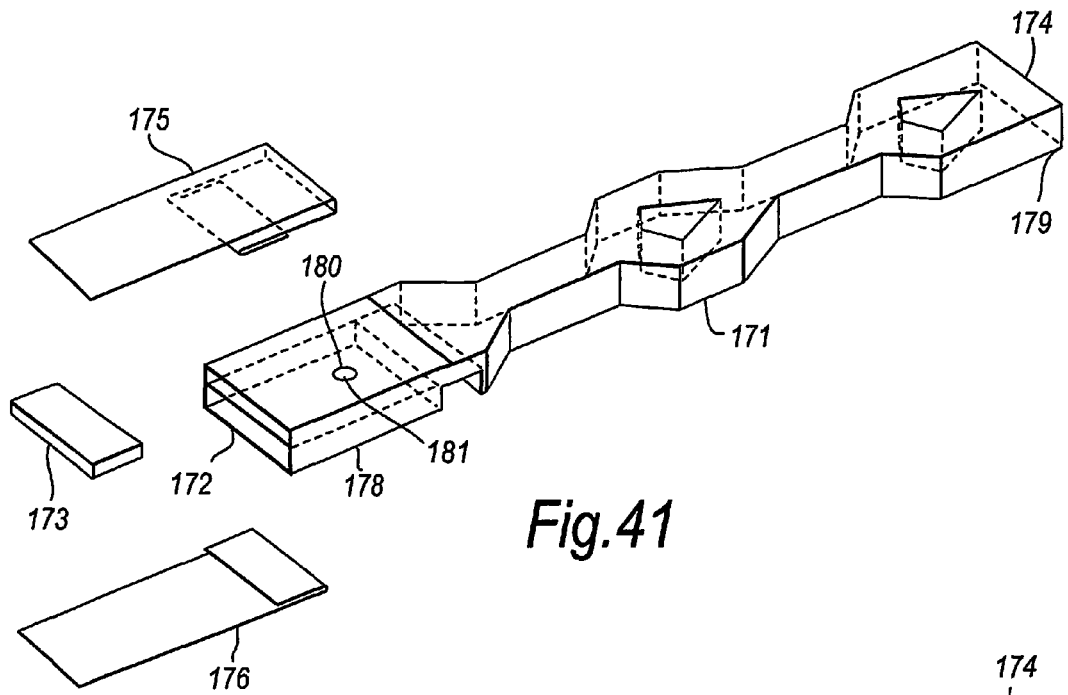
FIG. 41 is an exploded view of an eleventh preferred embodiment of the present invention.
Figure 42:
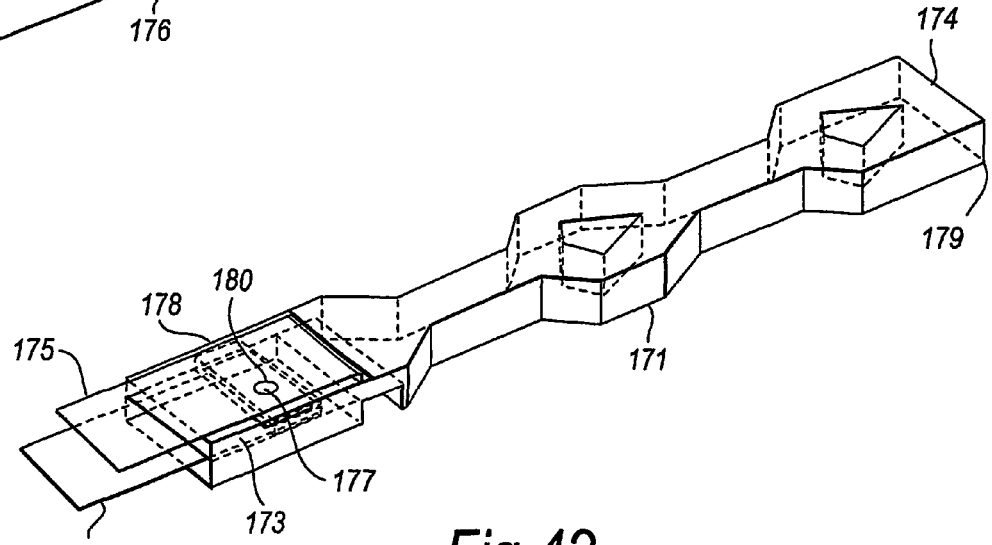
FIG. 42 is a perspective view of the inhalation device in FIG. 41 when assembled.

FIG. 40 depicts a modified embodiment of the applicants' inhalation device known as the TURBUHALER® which comprises a drying agent in the lower or distal end. The inhalation device operates substantially in the manner described in WO 98/41256 and differs in that a block of drying agent is located adjacent to the main air inlet which is now in the distal end rather than in the side of the device. The drying agent dries the air drawn by a user into the inhalation device prior to contact with the powdered medicament in the dosing means. The components of the inhalation device will only be described briefly since a full description is available by reference to WO 98/41256.

The inhalation device comprises a suction tube 151 having a distal end 158 and a proximal end 159. The user primes the inhalation device for use by rotating a gripping portion 160 which moves a dosing means 161 in the form of a plate such that a dose of powdered medicament sits in the air passage 162 passing between the distal and proximal ends 158,159 of the inhalation device. When the user inhales from the proximal end 159, air will be drawn through the distal end 158 via main air inlet 152, through the drying agent 153 and up into air passage 162 entraining the dose of powdered medicament in the dried stream of air. The powder then passes through a helical passage 163 and leaves the inhalation device via air outlet 154 into the mouth of the user. Although desiccants have been used in this type of inhalation device for drying the powdered medicament, a drying agent has never been used for reducing humidity in the air drawn into the inhalation device.

A further embodiment of the present invention is depicted in FIGS. 41 to 44. This is a modification of the applicants' inhalation device known as the MONOHALER® described in WO 92/04069. The inhalation device comprises a suction tube 171 having a distal end 178 and a proximal end 179. The distal end 178 comprises the air inlet 172 and the proximal end 179 which forms the mouthpiece comprises an air outlet 174. The inhalation device further comprises a drying agent 173 located inside the suction tube 171 just inside the air inlet 172. A single dose of powdered medicament 177 in a cavity 180 is sealed by lower foil strip 175 and upper foil strip 176 in an airtight way until the user wishes to inhale the powder. The foil strips 175 and 176 are simply pulled away from the distal end 178 (foil strip 176 passing through a hole 182) and the powder 177 is then exposed and can be inhaled when the user breathes in from the proximal end 179. Airflow arrows are included in FIGS. 43 and 44.

Figure 43:
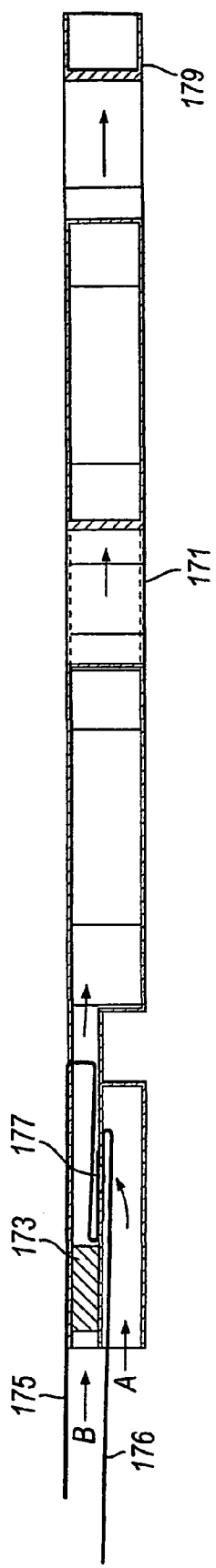
FIG. 43 is a sectional view through the inhalation device in FIG. 41.
Figure 44:
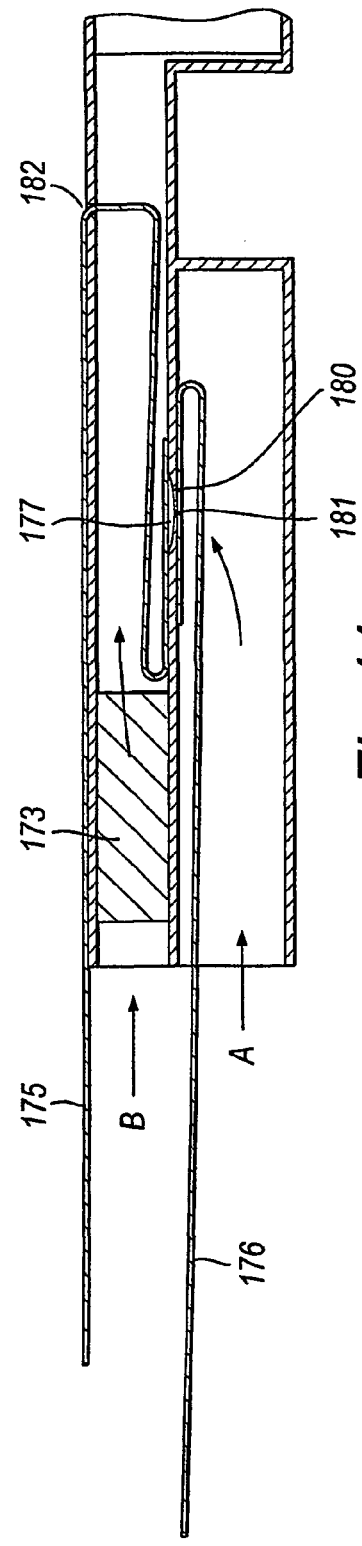
FIG. 44 is an enlarged view of the distal end of the inhalation device in FIG. 43.

FIG. 44 is an enlarged view of the distal end 178 of the inhalation device in FIG. 43. Details of the lower and upper foil strips 175, 176 can be seen. When these strips are removed air can flow into the inhalation device both above and below the powdered medicament 177. The airflow A below the powdered medicament 177 is introduced to ease release of the powder into the airflow B which has been dried on passing through the drying agent 173. The volume of airflow A is minimal in comparison to the volume of airflow B and is, therefore, not significant with regard to any contact it makes with the powdered medicament 177 when passing through a small hole 181 in the bottom of cavity 180. Drying of airflow A is not necessary since the main objective of this airflow is to prevent vacuum effects holding the powdered medicament 177 in the cavity 180. However, a further block of drying agent could be located in airflow A if a detrimental effect were to occur. Thereafter, the powder travels with the airflow through the suction tube 171 to the air outlet 179 into the mouth of the user. The specific design of a suction tube similar to suction tube 171 is described in detail in WO 92/04069 although the design in this embodiment has been modified slightly.

The invention claimed is:

1. An inhalation device for delivery of a powdered medicament comprising a suction channel and a plurality of doses of powdered medicament, the suction channel having a distal end and a proximal end with an air passage therethrough, the distal end having an air inlet and the proximal end having an air outlet which forms a mouthpiece of the device, wherein the inhalation device further comprises a means for drying air drawn by a user into the inhalation device prior to contact with the powdered medicament such that a dose of powdered medicament will be dispersed in dried air for delivery at the proximal end, wherein the means for drying air is located outside the suction channel such that air is dried prior to entering the air inlet and a means for metered dosing of the powdered medicament, wherein the means for dosing is configured to meter a predetermined amount of powdered medicament per dose, independent of the air flow drawn into the inhalation device by the user.

2. An inhalation device as claimed in claim 1, wherein at least part of the volume of the air drawn by the user into the inhalation device passes through the means for drying the air prior to contact with the powdered medicament.

3. An inhalation device as claimed in claim 1, wherein the suction channel is in the form of a suction tube and the powdered medicament is located outside the suction tube.

4. An inhalation device as claimed in claim 3, wherein the powdered medicament is contained in a blister pack having one or more blisters and the suction tube is constructed such that the distal end can penetrate a blister.

5. An inhalation device as claimed in claim 4, wherein the inhalation device further comprises a housing having one or more channels therein for directing air inhaled by the user to the air inlet.

6. An inhalation device as claimed in claim 5, wherein the means for drying the air is located between the housing and the air inlet.

7. An inhalation device as claimed in claim 3 wherein the means for drying air includes a drying box in fluid communication with the suction tube via an elongated conduit.

8. An inhalation device as claimed in claim 7 wherein the conduit includes a valve constructed to prevent airflow from the suction tube into the drying box.

9. An inhalation device as claimed in claim 3 wherein the means for drying air surrounds the suction tube.

10. An inhalation device as claimed in claim 1 wherein the means for drying air comprises a drying agent disposed in a container with the powdered medicament.

11. An inhalation device as claimed in claim 1 wherein the means for drying air includes an air intake, and means for sealing the air intake when the device is not in use.

12. An inhalation device as claimed in claim 11 wherein the means for sealing is constructed to seal the air intake after inhalation is complete or after a predetermined time or predetermined volume of airflow.

13. An inhalation device as claimed in claim 11 wherein the device includes a bypass intake, not in fluid communication with the means for drying air, that remains open after the air intake is sealed.

14. An inhalation device as claimed in claim 11 wherein the means for sealing includes hinged flaps.

15. An inhalation device as claimed in claim 14 wherein the flaps are operated by a motor.

16. An inhalation device as claimed in claim 1 wherein the powdered medicament is separated from the drying means by a seal.

17. An inhalation device for delivery of a powdered medicament comprising a suction channel and one or more doses of powdered medicament, the suction channel having a distal end and a proximal end with an air passage therethrough, the distal end having an air inlet and the proximal end having an air outlet which forms a mouthpiece of the device, a means for drying air drawn by a user into the inhalation device prior to contact with the powdered medicament such that a dose of powdered medicament will be dispersed in dried air for delivery at the proximal end, and a means for metered dosing of the powdered medicament, wherein the means for dosing is configured to meter a predetermined amount of powdered medicament per dose, independent of the air flow drawn into the inhalation device by the user, and wherein the suction channel includes a suction tube, and the powdered medicament is located outside the suction tube.

18. An inhalation device for delivery of a powdered medicament comprising a suction channel and one or more doses of powdered medicament, the suction channel having a distal end and a proximal end with an air passage therethrough, the distal end having an air inlet and the proximal end having an air outlet which forms the mouthpiece of the device, a means for drying air drawn by a user into the inhalation device prior to contact with the aggregated powdered medicament such that a dose of powdered medicament will be dispersed in dried air for delivery at the proximal end, and a means for metered dosing of the powdered medicament, wherein the means for dosing is configured to meter a predetermined amount of powdered medicament per dose, independent of the air flow drawn into the inhalation device by the user.

19. An inhalation device for delivery of a powdered medicament comprising a suction channel and one or more doses of powdered medicament, the suction channel having a distal end and a proximal end with an air passage therethrough, the distal end having an air inlet and the proximal end having an air outlet which forms a mouthpiece of the device, a means for drying air drawn by a user into the inhalation device prior to contact with the powdered medicament such that a dose of powdered medicament will be dispersed in dried air for delivery at the proximal end, a means for metered dosing of the powdered medicament, wherein the means for dosing is configured to meter a predetermined amount of powdered medicament per dose, independent of the air flow drawn into the inhalation device by the user, and a bypass whereby some of the air drawn into the inhalation device by the user is allowed to bypass the means for drying air.

\* \* \* \* \*